(12) United States Patent
Harper et al.

(10) Patent No.: US 10,301,264 B2
(45) Date of Patent: *May 28, 2019

(54) COMPOUNDS USEFUL FOR TREATING OCULAR NEOVASCULAN

(71) Applicant: The University of Nottingham, Nottinghamshire (GB)

(72) Inventors: Steven James Harper, Gwent (GB); David Owen Bates, Nottinghamshire (GB); Melissa Gammons, Cornwall (GB); Jonathan Morris, New South Wales (AU)

(73) Assignee: The University of Nottingham, Nottinghamshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/436,727

(22) PCT Filed: Oct. 17, 2013

(86) PCT No.: PCT/GB2013/052716
§ 371 (c)(1),
(2) Date: Apr. 17, 2015

(87) PCT Pub. No.: WO2014/060763
PCT Pub. Date: Apr. 24, 2014

(65) Prior Publication Data
US 2015/0274668 A1    Oct. 1, 2015

(30) Foreign Application Priority Data

Oct. 17, 2012 (GB) .................. 1218676.3
Oct. 18, 2012 (GB) .................. 1218758.9
Mar. 15, 2013 (GB) .................. 1304694.1

(51) Int. Cl.
| | | |
|---|---|---|
| C07D 405/12 | (2006.01) |
| C07D 405/14 | (2006.01) |
| A61K 31/341 | (2006.01) |
| A61K 31/496 | (2006.01) |
| C07D 213/81 | (2006.01) |
| A61K 31/35 | (2006.01) |
| A61K 31/395 | (2006.01) |
| A61K 31/44 | (2006.01) |
| C07D 213/82 | (2006.01) |
| C07D 307/68 | (2006.01) |

(52) U.S. Cl.
CPC .......... *C07D 213/81* (2013.01); *A61K 31/341* (2013.01); *A61K 31/35* (2013.01); *A61K 31/395* (2013.01); *A61K 31/44* (2013.01); *C07D 213/82* (2013.01); *C07D 307/68* (2013.01); *C07D 405/12* (2013.01); *C07D 405/14* (2013.01)

(58) Field of Classification Search
CPC .. C07D 405/12; C07D 405/14; A61K 31/341; A61K 31/496

USPC ......... 549/483; 544/395; 514/255.03, 252.13
See application file for complete search history.

(56) References Cited

U.S. PATENT DOCUMENTS

| | | | |
|---|---|---|---|
| 3,352,663 A | 11/1967 | Freund et al. | |
| 7,569,536 B2* | 8/2009 | Hagiwara | A61K 31/4409 424/9.1 |
| 9,695,160 B2* | 7/2017 | Bates | A61K 31/496 |
| 2006/0009453 A1* | 1/2006 | Geuns-Meyer | C07D 213/73 514/241 |

FOREIGN PATENT DOCUMENTS

| | | | |
|---|---|---|---|
| CN | 101422603 | 5/2009 | |
| DE | 1187420 B | 2/1965 | |
| EP | 1712242 A1 * | 10/2006 | ......... A61K 31/4409 |
| EP | 2279750 A1 | 2/2011 | |
| WO | 0020358 | 4/2000 | |
| WO | 2005063293 A1 | 7/2005 | |
| WO | WO-2006044823 A2 * | 4/2006 | ......... C07D 213/74 |
| WO | WO-2007072041 A1 * | 6/2007 | ......... C07C 235/56 |
| WO | 2008080056 A2 | 7/2008 | |
| WO | 2008110777 A2 | 9/2008 | |
| WO | 2009011850 | 1/2009 | |
| WO | 2009020198 A1 | 2/2009 | |
| WO | 2009106855 A1 | 9/2009 | |
| WO | 2010058227 A2 | 5/2010 | |
| WO | 2011036429 A1 | 3/2011 | |
| WO | 2011134898 A1 | 11/2011 | |
| WO | 2011148200 A1 | 12/2011 | |
| WO | WO 2012058176 A1 * | 5/2012 | ......... A61K 31/425 |

OTHER PUBLICATIONS

Gammons, M., O. Fedorov, D. Ivison, C. Du, T. Clark, C. Hopkins, M. Hagiwara, A. Dick, R. Cox, S. Harper, J. Hancox, S. Knapp, and D. Bates "Topical Antiangiogenic SRPK1 Inhibitors Reduce Choroidal Neovascularization in Rodent Models of Exudative AMD" IOVS (2013), 54 (9), pp. 6052-6062.*

Qui, Y., C. Hoareau-Aveilla, S. Oltean, S. Harper, and D. Bates, "The anti-angiogenic isoforms of VEGF in health and disease" Biochem. Soc. Trans. (2009), 37: pp. 1207-1213.*

Takahashi et al. "Topical Nepafenac Inhibits Ocular Neovascularization" IOVS (2003), 44 (1), pp. 409-415.*

Amin, E. M. et al. (2011) 'WT1 Mutants Reveal SRPK1 to Be a Downstream Angiogenesis Target by Altering VEGF Splicing', Cancer Cell, 20(6), 768-780.

Anderson, D. H. et al. (2002) 'Perspective—A role for local inflammation in the formation of drusen in the aging eye', American Journal of Ophthalmology, 134(3), 411-431.

(Continued)

*Primary Examiner* — Matthew P Coughlin
*Assistant Examiner* — Sagar Patel
(74) *Attorney, Agent, or Firm* — Hovey Williams LLP

(57) ABSTRACT

Anti-angiogenic treatments, treatments of hyperpermeability disorders, treatments of neuropathic and neurodegenerative disorders, pain treatments, methods of reducing the risk of pre-eclampsia and compounds for use in such methods are described.

9 Claims, 15 Drawing Sheets

Specification includes a Sequence Listing.

(56) References Cited

OTHER PUBLICATIONS

Aubol, B. E et al. (2003) 'Processive phosphorylation of alternative splicing factor/splicing factor 2', Proceedings of the National Academy of Sciences of the United States of America, 100(22), 12601-12606.
Bates, D. O. et al. (2002) 'VEGF(165)b, an inhibitory splice variant of vascular endothelial growth factor, is down-regulated in renal cell carcinoma', Cancer Research, 62(14), 4123-4131.
Brown D. M. et al. (2006) 'Ranibizumab versus verteporfin for neovascular age-related macular degeneration', New England Journal of Medicine, 355(14), 1432-1444.
Bundgaard, H., Advanced Drug Delivery Reviews, 8, p. I-38, 1992.
Bundgaard, H., 'Glycolamide esters as biolabile prodrugs of carboxylic acid agents: Synthesis, stability, bioconversion, and physicochemical properties' Journal of Pharmaceutical Sciences, 77, p. 285,1988.
Brown, D. M. et al. (2009) 'Ranibizumab versus Verteporfin Photodynamic Therapy for Neovascular Age-Related Macular Degeneration: Two-Year Results of the ANCHOR Study', Ophthalmology, 116(1), 57-65.
Caires, K. C. et al. (2012) 'VEGFA Family Isoforms Regulate Spermatogonial Stem Cell Homeostasis in Vivo', Endocrinology, 153(2).
Campochiaro, et al. (2006) 'Adenoviral vector-delivered pigment epithelium-derived factor for neovascular age-related macular degeneration: Results of a phase I clinical trial', Human Gene Therapy, 17(2), 167-176.
Das, A. et al. (2003) 'Angiopoietin/Tek interactions regulate MMP-9 expression and retinal neovascularization', Laboratory Investigation, 83(11), 1637-1645.
Doukas, J. et al. (2008) 'Topical administration of a multi-targeted kinase inhibitor suppresses choroidal neovascularization and retinal edema', Journal of Cellular Physiology, 216(1), 29-37.
Dvorak, H. F. et al. (1995) 'Vascular-permeability factor vascular endothelial growth-factor, microvascular hyperpermeability, and angiogenesis', American Journal of Pathology, 146(5), 1029-1039.
Ferris, F. L. et al. (1984) 'Age-related macular degeneration and blindness due to neovascular maculopathy', Archives of Ophthalmology, 102(11), 1640-1642.
Fine, S. L. et al. (2000) 'Drug therapy: Age-related macular degeneration', New England Journal of Medicine, 342(7), 483-492.
Fukuhara, T. et al. (2006) 'Utilization of host SR protein kinases and RNA-splicing machinery during viral replication', Proceedings of the National Academy of Sciences of the United States of America, 103(30), 11329-11333.
Gammons, M.V. et al. (2013) SRPK1 Inhibition Modulates VEGF Splicing to Reduce Pathological Neovascularization in a Rat Model of Retinopathy of Prematurity Invest. Ophthalmol. Vis. Sci. vol. 54(8) 5797-5806.
Gammons, M.V. et al. (2013) Topical Antiangiogenic SRPK1 Inhibitors Reduce Choroidal Neovascularization in Rodent Models of Exudative AMD Invest. Ophthalmol. Vis. Sci. 54(9) 6052-6062.
Geroski, D. H. et al. (2000) 'Drug delivery for posterior segment eye disease', Investigative Ophthalmology & Visual Science, 41(5), 961-964.
Good, T. J. et al. (2010) 'The role of endothelin in the pathophysiology of glaucoma', Expert Opinion on Therapeutic Targets, 14(6), 647-654.
Harris, S. et al. (2012) 'Do Anti-Angiogenic VEGF (VEGFxxxb) Isoforms Exist? A Cautionary Tale', Plos One, 7(5).
Higuchi, T. et al.; 'Pro-drugs as Novel Delivery Systems', in Edward B. Roche, ed., Symposium Series, and Bioreversible Carriers in Drug Design, vol. 14 (A. C. S., American Pharmaceutical Association and Pergamon Press) 1987.
Houck, K. A. et al. (1991) 'The vascular endothelial growth-factor family—identification of a 4th molecular-species and characterization of alternative splicing of ma', Molecular Endocrinology, 5(12), 1806-1814.

Hua, J. et al. (2010) 'Recombinant Human VEGF(165)b Inhibits Experimental Choroidal Neovascularization', Investigative Ophthalmology & Visual Science, 51(8), 4282-4288.
Ishida, S. et al. (2003) 'VEGF(164)-mediated inflammation is required for pathological, but not physiological, ischemia-induced retinal neovascularization', Journal of Experimental Medicine, 198(3), 483-489.
Jager, R. D.et al.(2004) 'Risks of intravitreous injection: A comprehensive review', Retina—the Journal of Retinal and Vitreous Diseases, 24(5), 676-698.
Jingjing, L. et al. (1999) 'Human Muller cells express VEGF183, a novel spliced variant of vascular endothelial growth factor', Iovs, 40(3), 752-759 • Kakeya, N. et al., Chem. Pharm. Bull., 32, p. 692,1984.
Kakeya, N. et al., Chem. Pharm. Bull., 32, p. 692,1984.
Keyt, B. A. et al. (1996) 'Identification of vascular endothelial growth factor determinants for binding KDR and FLT-1 receptors— Generation of receptor-selective VEGF variants by site-directed mutagenesis', Journal of Biological Chemistry, 271(10), 5638-5646.
Koresawa et al. (2004), 'High-Throughput Screening with Quantitation of ATP Consumption: A Universal Non-Radioisotope Homogenous Assay for Protein Kinase' Assay and Drug Development Technologies, 2(2).
Leung, D. W. et al. (1989) 'Vascular endothelial growth-factor is a secreted angiogenic mitogen', Science, 246(4935), 1306-1309.
Magnussen, A. L. et al. (2010) 'VEGF-A(165)b Is Cytoprotective and Antiangiogenic in the Retina', Investigative Ophthalmology & Visual Science, 51(8), 4273-4281.
McFee, R. M. et al. (2012) 'The balance of proangiogenic and antiangiogenic VEGFA isoforms regulate follicle development', Cell and Tissue Research, 349(3).
Mineur, P. et al. (2007) 'Newly identified biologically active and proteolysis-resistant VEGF-A isoform VEGF111 is induced by genotoxic agents', Journal of Cell Biology, 179(6), 1261-1273.
Neufeld, G. et al. (1999) 'Vascular endothelial growth factor (VEGF) and its receptors', Faseb Journal, 13(1), 9-22.
Ngo, J. C. K. et al. (2005) 'Interplay between SRPK and Clk/Sty kinases in phosphorylation of the splicing factor ASF/SF2 is regulated by a docking motif in ASF/SF2', Molecular Cell, 20(1), 77-89.
Nowak, D. G. (2010) 'Regulation of Vascular Endothelial Growth Factor (VEGF) Splicing from Pro-angiogenic to Anti-angiogenic Isoforms a novel therapeutic strategy for angiogenesis', Journal of Biological Chemistry, 285(8), 5532-5540.
Nowak, D. G. et al. (2008) 'Expression of pro- and anti-angiogenic isoforms of VEGF is differentially regulated by splicing and growth factors', Journal of Cell Science, 121(20), 3487-3495.
Perrin, R. M. et al. (2005) 'Diabetic retinopathy is associated with a switch in splicing from anti- to pro-angiogenic isoforms of vascular endothelial growth factor', Diabetologia, 48(11), 2422-2427.
Pritchard-Jones, R. O. et al. (2007) 'Expression of VEGF(xxx)b, the inhibitory isoforms of VEGF, in malignant melanoma', British Journal of Cancer, 97(2), 223-230.
Rennel, E. S. et al. (2011) 'A Human Neutralizing Antibody Specific to Ang-2 Inhibits Ocular Angiogenesis', Microcirculation, 18(7).
Rosefelf, P. J. et al. (2006) 'Ranibizumab: Phase III clinical trial results', Ophthalmology clinics of North America, 19(3), 361-72.
Sanford, J. R. et al. (2005a) 'Reversible phosphorylation differentially affects nuclear and cytoplasmic functons of splicing factor 2/alternative splicing factor', Proceedings of the National Academy of Sciences of the United States of America, 102(42), 15042-15047.
Schmidt-Erfurth, U. et al. (2011) 'Efficacy and Safety of Monthly versus Quarterly Ranibizumab Treatment in Neovascular Age-related Macular Degeneration: The EXCITE Study', Ophthalmology, 118(5).
Spilsbury, K. et al. (2000) 'Overexpression of vascular endothelial growth factor (VEGF) in the retinal pigment epithelium leads to the development of choroidal neovascularization', American Journal of Pathology, 157(1), 135-144.
Stalmans, I. et al. (2002) 'Arteriolar and venular patterning in retinas of mice selectively expressing VEGF isoforms', Journal of Clinical Investigation, 109(3).

(56) References Cited

OTHER PUBLICATIONS

Tischer, E. et al. (1989) 'Vascular endothelial growth-factor—a new member of the platelet-derived growth-factor gene family', Biochemical and Biophysical Research Communications 165(3), 1198-1206.

Varey, A. et al. (2008) 'VEGF(165)b, an antiangiogenic VEGF-A isoform, binds and inhibits bevacizumab treatment in experimental colorectal carcinoma: balance of pro- and antiangiogenic VEGF-A isoforms has implications for therapy', British Journal of Cancer, 98(8), 1366-1379.

Velazquez-Dones, A. et al. (2005) 'Mass spectrometric and kinetic analysis of ASF/SF2 phosphorylation by SRPK1 and Clk/Sty', Journal of Biological Chemistry, 280(50), 41761-41768.

Woolard, J. et al. (2004) 'VEGF(165)b, an inhibitory vascular endothelial growth factor splice variant: Mechanism of action, in vivo effect on angiogenesis and endogenous protein expression', Cancer Research, 64(21), 7822-7835.

Xu, J. et al. (2011) 'The evolution of alternative splicing exons in vascular endothelial growth factor A', Gene, 487(2).

Zhao, M., et al. (2011) 'Expression of pro- and anti-angiogenic isoforms of VEGF in the mouse model of oxygen-induced retinopathy', Experimental Eye Research, 93(6), 921-926.

Bundgaard, H., (ed.) Design of Prodrugs (Elsevier, 1985).

International Search Report from PCT/GB2013/052716 dated Feb. 11, 2014 (4 pages).

Office Action in related Australian Patent Application Serial No. 2013333657, dated Apr. 11, 2017, 4 pages.

Office Action in related Chinese Patent Application No. 201380065738 dated Jan. 9, 2017, machine translation attached.

Office Action in corresponding Japanese Patent Application Serial No. 2015-537351, dated Sep. 26, 2017 (English translation attached).

Database Registry, 2011, RN: 1349022-02-1 1125444-51-0 1125443-45-9 1026959-84-1 848057-98-7; Retrieved from STN international [online]; retrieved on Sep. 19, 2017.

Oltean, et al., "SRPK1 inhibition in vivo: modulation of VEGF splicing and potential treatment for multiple diseases", Biochemical Society Transactions, 2012, 40(4), 831-835.

Horak, et al., "Antimicrobial and antifungal activity of 5-aryl-2-furancarboxamides", Farmatsevtichnii Zhurnal (Kiev, Ukraine), 2009, (1), 100-105.

* cited by examiner

SEQUENCE LISTING

```
<160> NUMBER OF SEQ ID NOS: 5

<210> SEQ ID NO 1
<211> LENGTH: 29
<212> TYPE: PRT
<213> ORGANISM: Artificial Sequence
<220> FEATURE:
<223> OTHER INFORMATION: SRSF1 RS PEPTIDE

<400> SEQUENCE: 1

Arg Ser Pro Ser Tyr Gly Arg Ser Arg Ser Arg Ser Arg Ser Arg Ser
1               5                   10                  15

Arg Ser Arg Ser Arg Ser Asn Ser Arg Ser Arg Ser Tyr
            20                  25

<210> SEQ ID NO 2
<211> LENGTH: 21
<212> TYPE: DNA
<213> ORGANISM: Artificial Sequence
<220> FEATURE:
<223> OTHER INFORMATION: PRIMER

<400> SEQUENCE: 2
ggcagcttga gttaaacgaa c                                             21

<210> SEQ ID NO 3
<211> LENGTH: 25
<212> TYPE: DNA
<213> ORGANISM: Artificial Sequence
<220> FEATURE:
<223> OTHER INFORMATION: PRIMER

<400> SEQUENCE: 3
atggatccgt atcagtcttt cctgg                                         25

<210> SEQ ID NO 4
<211> LENGTH: 22
<212> TYPE: DNA
<213> ORGANISM: Artificial Sequence
<220> FEATURE:
<223> OTHER INFORMATION: PRIMER

<400> SEQUENCE: 4
cacccactcc tccacctttg ac                                            22

<210> SEQ ID NO 5
<211> LENGTH: 22
<212> TYPE: DNA
```

```
<213> ORGANISM: Artificial Sequence
<220> FEATURE:
<223> OTHER INFORMATION: PRIMER

<400> SEQUENCE: 5
gtccaccacc ctgttgctgt ag                                           22
```

COMPOUNDS USEFUL FOR TREATING OCULAR NEOVASCULAN

RELATED APPLICATIONS

This application is the National Stage of International Patent Application No. PCT/GB2013/052716, filed Oct. 17, 2013, which is hereby incorporated by reference in its entirety, and which claims priority to Great Britain Patent Application Nos. 1218676.3, filed Oct. 17, 2012, 1218758.9, filed Oct. 18, 2012, and 1304694.1, filed Mar. 15, 2013.

SEQUENCE LISTING

The sequences listed in the accompanying Sequence Listing are presented in accordance with 37 C.F.R. 1.822. The Sequence Listing is submitted as an ASCII computer readable text file, which is incorporated by reference herein.

FIELD OF THE INVENTION

The present invention relates to anti-angiogenic treatments and compounds for use in anti-angiogenic treatments, particularly of conditions characterised by neovascularisation such as, for example, age-related macular degeneration.

The present invention also relates to treatments of hyperpermeability disorders and compounds for use in treating hyperpermeability disorders.

The present invention also relates to treatments of neuropathic and neurodegenerative disorders and compounds for use in treating neuropathic and neurodegenerative disorders, such as, for example, Alzheimer's disease.

The present invention also relates to pain treatments, and compounds for use in treating pain.

The present invention also relates to methods of reducing the risk of pre-eclampsia, and compounds for use in such methods.

BACKGROUND TO THE INVENTION

Age-related macular degeneration (AMD), a disease causing vision loss that affects the central area of the macula, is the leading cause of blindness in people over 50 years of age (Bressler, 2004). Exudative AMD is the most severe form of AMD (Ferris et al., 1984) primarily arising from the choroidal circulation beneath the macula and characterized by choroidal neovascularization (CNV). CNV, the abnormal growth of new vessels from the choroid into the retinal pigmented epithelium (RPE) (Patz et al., 1977), is thought to lead to visual loss due to the leakage of blood and serous fluid beneath the RPE that eventually leads to loss of photoreceptors, retinal detachment and dense macular scarring (Fine et al., 2000; Campochiaro et al., 2006). Vascular endothelial growth factor (VEGF), a key factor in angiogenesis and vascular leakage (Dvorak et al., 1995) is up-regulated during the progression of CNV (D'Amore, 1994; Spilsbury et al., 2000; Anderson et al., 2002; Das et al., 2003) and has become the lead therapeutic target for the treatment of exudative-AMD.

VEGF is a complex gene that is alternatively spliced to form a family of multiple isoforms (Leung et al., 1989; Jingiing et al., 1999), each isoform differing in biological property, activity and function (Houck et al., 1991). Most cells commonly express isoforms $VEGF_{121}$, $VEGF_{165}$, and $VEGF_{189}$, whereas $VEGF_{145}$ and $VEGF_{206}$ are comparatively rare. The majority of VEGF isoforms contain exons 1-5 (the exception being $VEGF_{111}$ (Mineur et al., 2007)) but differing portions of exons 6 and 7 that encode heparin sulphate (HS) binding domains. Alterations in the usage of these exons changes the biological properties of alternatively spliced isoforms such as their ability to bind to cell-surface heparan-sulfate proteoglycans and release angiogenic factors (Tischer et al., 1991; Neufeld et al., 1999).

In 2002 differential splicing of the eighth exon was demonstrated from a proximal splice site (PSS) to a distal splice site (DSS) 66 bases downstream (Bates et al., 2002; Woolard et al., 2004). Alternative splicing in this region generated a second family of isofolins ($VEGF_{xxx}b$), noted for their anti-angiogenic properties (Perrin et al., 2005). WO 03/02105, the contents of which are incorporated herein by reference in its entirety describes the alternatively spliced isoforms, and their therapeutic significance.

During pathological angiogenesis pro-angiogenic isoforms are selectively upregulated (Bates et al., 2002; Varey et al., 2008; Pritchard-Jones et al., 2007), suggesting $VEGF_{xxx}$ and $VEGF_{xxx}b$ may have separate regulatory pathways. These anti-angiogenic isoforms, such as $VEGF_{165}b$ and $VEGF_{121}b$ have been shown to be potently anti-angiogenic in animal models of retinal and choroidal neovascularisation, following intra-ocular injection (Hua et al 2008), and result in both endothelial and retinal epithelial cell cytoprotection (Magnussen et al 2010).

The first therapy to be FDA approved for the treatment of neovascular AMD in December 2004 was a $VEGF_{165}$, $VEGF_{189}$ and $VEGF_{206}$ specific aptamer, Pegaptanib Sodium (Macugen). During clinical trials pegaptinib dose-dependently reduced the risk of severe visual acuity loss and slowed the progression of neovascular AMD (Gragoudas et al., 2004), but did not result in significant improvement in vision. In 2006 Ranibizumab (Lucentis), a novel humanized anti-VEGF antibody fragment, was FDA approved for the treatment of neovascular AMD. Its approval was based on the results of three clinical trials where, approximately 95% of patients treated monthly with Lucentis 0.5 mg maintained visual acuity (defined as the loss of <15 letters) and ≤40% improved vision (defined as the gain of ≥15 letters) at one year compared with 11% in the sham control treated group (Rosenfeld et al., 2006; Brown et al., 2006; Brown et al., 2009). Current treatment regimes require Lucentis administration by intra-ocular injection as often as monthly (Brown et al., 2009; Schmidt-Erfuth et al., 2011). Such intraocular injections result in increased intraocular pressure (Good et al., 2010) and a risk, albeit minor, of endopthalmitis and other severe adverse effects (Jager et al., 2004). Furthermore, bevicizumab (Avastin), an anti-VEGF antibody from which Lucentis was derived, was shown to bind $VEGF_{165}b$ with equal potency to $VEGF_{165}$, thus targeting both pro and anti-angiogenic VEGF isoforms (Varey et al 2008).

As both the anti-angiogenic and angiogenic isoforms of VEGF are derived from the same gene, the control of isoform family is a result of the control of alternative splicing. We have recently identified some of the pathways that control the splicing of VEGF at the proximal splice site, implicating the RNA binding protein SRSF1 (Nowak et al., 2008; Amin et al., 2011) and its kinase SRPK1 (Sanford et al., 2005) as key requirements for the decision by cells to use the proximal splice site, and hence generate pro-angiogenic isoforms of VEGF (Nowak et al., 2008; Nowak et al., 2010). Knockdown of SRPK1 potently reduced VEGF mediated angiogenesis in vivo in tumours and inhibition of SRPK1 and 2 reduced angiogenesis in vivo (Amin et al., 2011).

WO 2008/11077, WO 2009/106855, WO 2010/058227, WO 2011/036429 and WO 2011/148200, the disclosures of which are incorporated herein by reference, describe therapeutic and other physiological uses of agents which direct expression in favour of the VEGF$_{xxx}$b isoforms. SRPK inhibitors can in principle constitute such agents.

WO 2005063293 describes a class of SRPK inhibitors including SRPIN340 and derivatives and analogues thereof.

The development of new agents for directing expression of VEGF$_{xxx}$b isoforms represents a new era not only in the treatment of, for example, neovascular AMD, but all other diseases in which VEGF$_{xxx}$b is implicated.

The present invention is based in part on new small molecule inhibitors targeting SRPK1 specifically for use as anti-angiogenic agents, neuroprotective agents, agents for use in treating or preventing hyperpermeability disorders, as agents for treating pain, and as agents for reducing the risk of, or treatment of, pre-eclampsia.

The present invention is also based at least in part on the surprising finding that low molecular weight compounds known to inhibit SRPK1 (e.g. SRPIN340 and derivatives and analogues thereof) could be used topically or in dose-dependent manner to inhibit CNV progression.

SUMMARY OF THE INVENTION

In a first aspect the invention provides a compound of Formula (I)

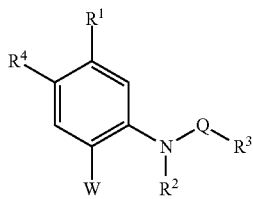

(I)

or a pharmaceutically acceptable salt, solvate, hydrate or prodrug thereof;
wherein:
$R^1$ represents a hydrogen atom, a $C_{1-6}$ alkyl group which may have one or more substituent, a $C_{2-6}$ alkenyl group which may have one or more substituent, a $C_{2-6}$ alkynyl group which may have one or more substituent, a $C_{6-10}$ aryl group which may have one or more substituent, a halogen atom, a nitro group, a cyano group, an azido group, a hydroxy group, a $C_{1-6}$ alkoxy group which may have one or more substituent, a $C_{1-6}$ alkylthio group which may have one or more substituent, a $C_{1-6}$ alkylsulfonyl group which may have one or more substituent, a carboxyl group, a formyl group, a $C_{1-6}$ alkoxycarbonyl group which may have one or more substituent, an acyl group, an acylamino group, or a sulfamoyl group;
$R^2$ represents a hydrogen atom, a $C_{1-6}$ alkyl group which may have one or more substituent, or an aryl group which may have one or more substituent;
$R^3$ represents a $C_{1-6}$ alkyl group which may have one or more substituent, a $C_{2-6}$ alkenyl group which may have one or more substituent, a $C_{6-10}$ aryl group which may have one or more substituent, a nitrogen-containing heterocycle which may have one or more substituent, an oxygen-containing heterocycle which may have one or more substituent, or a condensed aromatic heterocycle which may have one or more substituent;
$R^4$ represents a hydrogen atom or a halogen atom;
Q represents —C(O)—, —C(S)—, —SO$_2$— —C(S)NHC(O)—, —C(O)NHC(O)—, or C(O)NHC(S)—; and
W represents a hydrogen atom, amino, a $C_{1-6}$ alkyl group which may have one or more substituent, a $C_{6-10}$ aryl group which may have one or more substituent, a halogen atom, a hydroxy group, a $C_{1-6}$ alkoxy group which may have one or more substituent, a $C_{1-6}$ alkylthio group which may have one or more substituent, a nitrogen-containing heterocycle which may have one or more substituent, a condensed aromatic heterocycle which may have one or more substituent, or a group represented by the following formula (II):

(II)

wherein $R^5$ and $R^6$ are the same or different and each represents a hydrogen atom, a $C_{1-6}$ alkyl group which may have one or more substituent, a nitrogen-containing heterocycle which may have one or more substituent, a condensed aromatic heterocycle which may have one or more substituent, an acyl group, or an acylamino group;
or the above $R^5$ and $R^6$ together with the adjacent nitrogen atom may form a heterocycle which may have one or more substituent, and the heterocycle may be a condensed aromatic heterocycle which may have one or more substituent;
or the above $R^5$ and $R^6$ may be a cycloalkylidene amino group which may have one or more substituent, or an aromatic condensed cycloallcylidene group which may have one or more substituent;
for use in dose-dependent treatment or prevention of ocular neovascularisation.

The dose dependency is preferably a sigmoidal efficacy-dose relationship, e.g. of the type illustrated in FIG. 4 (left hand panel) of the accompanying drawings. The expression "ocular neovascularisation" includes within its scope diseases and disorders characterised by ocular neovascularisation, including for example choroidal neovascularisation such as age-related macular degeneration. The term "ocular neovascularisation" also includes within its scope diseases and disorders characterized by retinal neovascularisation.

In a second aspect the invention provides a compound of formula (I) or a pharmaceutically acceptable salt, solvate, hydrate or prodrug thereof for use in the topical treatment or prevention of ocular neovascularisation.

The first and second aspects of the invention also provide respective methods of treatment or prevention of ocular neovascularisation by administration of the compound of formula (I) to a subject in need of such treatment, and respective uses of a compound of formula (I) in the preparation of a medicament for treatment or prevention of ocular neovascularisation, as a dose-dependent treatment and/or as a topical treatment.

It is surprising and not expected from the prior art that the compounds used in the present invention enable dose-dependent treatment or prevention of ocular neovascularisation or topical treatment or prevention of ocular neovascularisation. Dose-dependent treatment is not inherently predictable, yet is highly desirable and beneficial for effective treatment.

The specific compounds of formula (I), and preferred or exemplified sub-classes of compounds of formula (I), as described in WO 2005/063293, and their pharmaceutically acceptable salts, solvates, hydrates and prodrugs, may be particularly mentioned for use in the present invention.

Further examples of the compounds of formula (I) that may be mentioned for use in the methods of the present invention are those in which $R^3$ is an oxygen-containing heterocycle which may have one or more substituent, or a 2- or 3- or 4-pyridyl group which may have one or more substituent. Preferred compounds include those in which $R^3$ is an oxygen-containing heterocycle substituted by a phenyl group or a 2- or 3- or 4-pyridyl group, which themselves may be further substituted as described herein. These compounds of formula (I) and their pharmaceutically acceptable salts, solvates, hydrates or prodrugs are new and as compounds per se (as well as their use in dose-dependent treatment or prevention of ocular neovascularisation and/or in the topical treatment or prevention of ocular neovascularisation) they constitute a further aspect of the present invention.

Pharmaceutical compositions comprising the novel compounds and the use of the novel compounds and pharmaceutical compositions comprising them in anti-angiogenic treatments (including the treatment and prevention of disorders and diseases characterised by abnormal or excessive angiogenesis), treatments of hyperpermeability disorders, treatments of neuropathic and neurodegenerative disorders, treatment of non-inflammatory pain and methods of reducing the risk of pre-eclampsia constitute further aspects of the present invention.

In the novel compounds of formula (I) in which $R^3$ is an oxygen-containing heterocycle which may have one or more substituent, the $R^3$ group may, for example be a furanyl group optionally substituted by $C_{1-6}$ alkyl, for example, methyl, for example 5-methyl-furan-2-yl, or a furanyl group optionally substituted by cyano, halo, nitro, formyl, 2- or 3- or 4-pyridyl or phenyl which each may have one or more substituents.

In the novel compounds of formula (I) in which $R^3$ is a 2- or 3- or 4-pyridyl group which may have one or more substituent, the 2- or 3- or 4-pyridyl group which may have one or more substituent may, for example, be an unsubstituted 3-pyridyl group (namely, where the nitrogen heteroatom of the pyridyl group is meta to the Q group).

As preferred examples of the novel compounds of formula (I) there may be mentioned those in which the W is an amino group or a morpholinyl group which may have one or more substituent, more particularly an unsubstituted morpholin-4-yl group, or a 1-piperazinyl group which may have one or more substituent, for example a 4-methyl substituent or an alkylamino substituent, more particularly a 4-(dimethylamino)ethyl or a 4-(dimethylamino)propyl substituent. In this group, there may be particularly mentioned the compounds wherein, in addition, $R^1$ is trifluoromethyl, $R^2$ and $R^4$ are both H.

For use in the first and second aspects of the present invention there may be mentioned as particularly preferred (a) the above compounds of formula (I) in which $R^3$ is an oxygen-containing heterocycle which may have one or more substituent, for example a phenyl substituent or a 2- or 3- or 4-pyridyl substituent, or a phenyl substituent or a 2- or 3- or 4-pyridyl group which may have one or more substituent, (b) SRPIN340, the formula of which is shown in FIG. 1 of the drawings, and (c) their pharmaceutically acceptable salts, solvates, hydrates or prodrugs. Examples of the compounds of formula (I) in which $R^3$ is an oxygen-containing heterocycle which may have one or more substituent, or a 2- or 3- or 4-pyridyl group which may have one or more substituent, include MVRL09 and MVRL10, the formulae of which are shown in FIG. 1 of the drawings, and MVRL16, MVRL17, SPHINX9, SPHINX10, SPHINX12, SPHINX13 and SPHINX14, the formulae of which are shown in Table 1. For the avoidance of doubt, the compounds MVRL10, MVRL16 and MVRL17 are also described as SPHINX, SPHINX6 and SPHINX7 respectively.

The compounds of Formula (I) and their pharmaceutically acceptable salts, solvates, hydrates and prodrugs may be further characterized by one or more of the following features, which are, whether individually or in any combination, combinable with any of the examples and preferences stated herein, or in WO 2005/063293, for the compounds:

1. $R^1$ may represent a trifluoromethyl group;
2. $R^3$ may represent an oxygen-containing heterocycle or a 2- or 3- or 4-pyridyl group;
3. $R^3$ may represent an oxygen-containing heterocycle substituted by a phenyl group or a 2- or 3- or 4-pyridyl group;
4. W may represent a 4-morpholino group which may have one or more substituents, or a 1-piperazinyl group which may have one or more substituents;
5. W may represent a 1-piperazinyl group or a 4-methyl-1-piperazinyl group or a 4-(2-(dimethylamino)ethyl)-1-piperazinyl group or a 4-(2-(dimethylamino)propyl)-1-piperazinyl group;
6. when $R^1$ is trifluoromethyl, $R^2$=$R^4$=H, $R^3$ is 4-(3-pyridyl)-furan-2-yl and Q is —C(O)—, then W is not the group represented by formula (II) wherein $R^5$ or $R^6$ is a $C_{1-6}$ alkyl group substituted by amino or substituted amino; and
7. when $R^2$=$R^4$=H, $R^3$ is 4-pyridyl, and W is N-piperidinyl and Q is —C(O)—, then $R^1$ is not hydrogen.

The compounds represented by formula (I) include, for example:

(1) such compounds in which the above $R^1$ is a hydrogen atom, a $C_{1-6}$ alkyl group, a halogenated $C_{1-6}$ alkyl group, or a halogen atom;
(2) such compounds in which the above $R^1$ is a trifluoromethyl group;
(3) such compounds in which the above $R^2$ is a hydrogen atom or a $C_{1-6}$ alkyl group;
(4) such compounds in which the above $R^2$ is a hydrogen atom;
(5) such compounds in which the above $R^3$ is a nitrogen-containing 5- to 10-membered heteroaryl ring having one or more substituents or an oxygen-containing 5- to 10-membered heteroaryl ring which may have substituents;
(6) such compounds in which the above $R^3$ is a a pyridyl ring or a furan ring which may have one or more substituents;
(7) such compounds in which the above $R^3$ is a 2- or 3- or 4-pyridyl ring;
(8) such compounds in which the above $R^3$ is furan ring which may have one or more substituents;
(9) such compounds in which the above $R^3$ is a furan ring substituted with a phenyl ring or a pyridyl ring;
(10) such compounds in which the above $R^4$ is a hydrogen atom;
(11) such compounds in which the above Q is —C(O)— or —C(O)NHC(S)—, where C(O) means that an oxygen atom is linked with a carbon atom via a double bond, and C(S) means that a sulfur atom is linked with a carbon atom via a double bond;
(12) such compounds in which the above Q is —C(O)—;

(13) such compounds in which the above W is represented by formula (II) wherein $R^5$ and $R^6$, together with the adjacent nitrogen atom, form a heterocyclic group which may have substituents;

(14) such compounds in which the above W is a 4- to 8-membered heterocyclic group having one nitrogen atom, which may have a $C_{1-6}$ alkyl group as a substituent, a 4- to 8-membered heterocyclic group comprising one nitrogen atom and one oxygen atom, which may have a $C_{1-6}$ alkyl group as a substituent, or a 4- to 8-membered heterocyclic group comprising two nitrogen atoms which may have a $C_{1-6}$ alkyl group as a substituent;

(15) such compounds in which the above W is a 4- to 8-membered heterocyclic group comprising one or two nitrogen atoms, which may have a $C_{1-6}$ alkyl group as a substituent;

(16) such compounds in which the above W is morpholino group, which may have a $C_{1-6}$ alkyl group as a substituent;

(17) such compounds in which the above W is a piperidinyl group or a piperazinyl group, which may have a $C_{1-6}$ alkyl group as a substituent; and

(18) such compounds in which the above W is a piperazinyl group with a $C_{1-6}$ alkyl group as a substituent.

In the compounds described above, $R^1$ is preferred in the order of (1) to (2), with (2) more preferred. $R^2$ is preferred in the order of (3) to (4), with (4) more preferred. $R^3$ is preferred in the order of (5) to (9), with (9) more preferred. Q is preferred in the order of (11) to (12), with (12) more preferred. W is preferred in the order of (13) to (18), with (18) more preferred.

More preferable compounds are represented by the above formula (I), and comprise any combination of substituent types, each of which is selected from (1) to (2) for $R^1$, (3) to (4) for $R^2$, (5) to (9) for $R^3$, (10) for $R^4$, (11) to (12) for Q, or (13) to (18) for W.

Thus, particularly mentioned compounds are those of Formula (I) in which:

$R^1$ is a trifluoromethyl group;

$R^2$ and $R^4$ are each hydrogen atoms;

$R^3$ is a a pyridyl ring or a furan ring, each of which may have one or more substituents;

Q is —C(O)—; and

W is a 4- to 8-membered heterocyclic group having one nitrogen atom, which may have one or more substituent, a 4- to 8-membered heterocyclic group comprising one nitrogen atom and one oxygen atom which may have one or more substituent, or a 4- to 8-membered heterocyclic group comprising two nitrogen atoms which may have one or more substituent.

Within this class of compounds, more preferred compounds are those of Formula (I), in which:

$R^1$ is a trifluoromethyl group;

R and $R^4$ are each hydrogen atoms;

$R^3$ is a a pyridyl ring or a furan ring, each of which may have one or more substituents;

Q is —C(O)—; and

W is a morpholino group, a piperidinyl group or a piperazinyl group, each of which may have one or more substituents.

Particularly mentioned compounds are those of Formula (Ia):

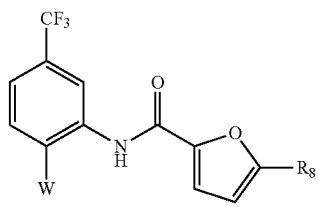

(Ia)

in which W is a 4- to 8-membered heterocyclic group having one nitrogen atom, which may have one or more substituent, a 4- to 8-membered heterocyclic group comprising one nitrogen atom and one oxygen atom which may have one or more substituent, or a 4- to 8-membered heterocyclic group comprising two nitrogen atoms which may have one or more substituent; and $R_8$ is hydrogen, a cyano group, a $C_{1-6}$ alkyl group, a phenyl group or a 2-, 3-, or 4-pyridyl ring. Substituents on the 4- to 8-membered heterocyclic groups defined by W may be those as defined elsewhere in connection with compounds of Formula (I).

DETAILED DESCRIPTION OF THE INVENTION

Anti-angiogenic Treatment

The anti-angiogenic treatment preferably includes the treatment or prevention of any disease or disorder associated with abnormal angiogenesis or abnormal over-production of pro-angiogenic VEGF isoforms ($VEGF_{xxx}$). Such diseases and disorders include, for example, vascular disease (e.g. vasoconstriction and disorders characterised by vasoconstriction, and cardiovascular disease), malignant and benign neoplasia (e.g. angiogenesis-dependent cancers, for example tumorous cancers), tumor metastasis, inflammatory disorders, diabetes, diabetic retinopathy and other complications of diabetes (e.g. diabetic neovascularisation), trachoma, retrolental hyperplasia, neovascular glaucoma, age-related macular degeneration, haemangioma, immune rejection of implanted corneal tissue, corneal angiogenesis associated with ocular injury or infection, Osler-Webber Syndrome, myocardial angiogenesis, wound granulation, telangiectasia, hemophiliac joints, angiofibroma, telangiectasia psoriasis scleroderma, pyogenic granuloma, coronary collaterals, ischemic limb angiogenesis, rubeosis, obesity, arthritis (e.g. rheumatoid arthritis), hematopoieses, vasculogenesis, gingivitis, atherosclerosis, endometriosis, neointimal hyperplasia, psoriasis, hirsutism and proliferative retinopathy. The anti-angiogenic treatment according to the present invention may also include non-therapeutic treatments performed on healthy subjects, for example to inhibit vascular development for cosmetic purposes. For further details on diseases and disorders associated with abnormal angiogenesis, and on anti-angiogenic treatments, see WO 2008/110777, the contents of which are incorporated herein by reference.

Microvascular Hyperpermeability Disorders, Disorders of Epithelial Cell Survival and Disorders of Fenestrations of Epithelial Filtration Membranes The compounds of the present invention, as SRPK1 inhibitors, may also be used as therapeutic agents in treating other disorders in which the alternatively spliced $VEGF_{xxx}b$ isoform has been implicated. For example, it has been shown in WO 2010/058227, the contents of which are incorporated herein by reference, that $VEGF_{xxx}b$ is active against a range of microvascular hyperpermeability disorders, disorders of epithelial cell survival and disorders of fenestrations of epithelial filtration membranes.

Microvascular hyperpermeability, disorders of regulation of the pro-angiogenic pro-permeability properties of VEGF$_{xxx}$ isoforms, disorders of epithelial cell survival and permeability, and/or disorders in the nature (for example the number density and/or size) of fenestrations of epithelial filtration membranes underlie a number of serious medical conditions.

Examples of such conditions include, for example, proteinuria, uraemia, microalbuminuria, hypoalbuminemia, renal hyperfiltration, nephrotic syndrome, renal failure, pulmonary hypertension, capillary hyperpermeability, microaneurysms, oedema and vascular complications of diabetes.

Examples of such vascular complications of diabetes include, for example, diabetic retinopathy, both proliferative and non-proliferative, and diabetic nephropathy. Vascular complications of diabetes can be associated with either Type I or Type II diabetes.

The loss of proteins from the blood can lead to further complications, for example thromboses, especially thromboses in the brain, and susceptibility to infections. Loss of natural proteins from the blood can seriously impair the efficacy of cancer therapies.

The microvascular hyperpermeability disorder may particularly be a renal disorder, for example a permeability disorder of the GFB, for example a permeability disorder of the podocytes.

Examples of disorders where treatment to support epithelial cell survival would be effective are as follows:

acute pulmonary fibrotic disease, adult respiratory distress syndrome, adult respiratory distress syndrome, advanced cancer, allergic respiratory disease, alveolar injury, angiogenesis, arthritis, ascites, asthma, asthma or edema following burns, atherosclerosis, autoimmune diseases, bone resorption, bullous disorder associated with subepidermal blister formation including bullous pemphigoid, cardiovascular condition, certain kidney diseases associated with proliferation of glomerular or mesangial cells, chronic and allergic inflammation, chronic lung disease, chronic occlusive pulmonary disease, cirrhosis, corneal angiogenisis, corneal disease, coronary and cerebral collateral vascularization, coronary restenosis, damage following heart disease, dermatitis herpetiformis, diabetes, diabetic nephropathy, diabetic retinopathy, endotoxic shock, erythema multiforme, fibrosis, glomerular nephritis, glomerulonophritis, graft rejection, gram negative sepsis, hemangioma, hepatic cirrhosis, hepatic failure, Herpes Zoster, host-versus-graft reaction (ischemia reperfusion injury and allograft rejections of kidney, liver, heart, and skin), impaired wound healing in infection, infection by Herpes simplex, infection from human immunodeficiency virus (HIV), inflammation, cancer, inflammatory bowel disease (Crohn's disease and ulcerative colitis), inflammatory conditions, in-stent restenosis, in-stent stenosis, ischemia, ischemic retinal-vein occlusion, ischemic retinopathy, Kaposi's sarcoma, keloid, liver disease during acute inflammation, lung allograft rejection (obliterative bronchitis), lymphoid malignancy, macular degeneration retinopathy of prematurity, myelodysplastic syndromes, myocardial angiogenesis, neovascular glaucoma, non-insulin-dependent diabetes mellitus (NIDDM), obliterative bronchiolitis, ocular conditions or diseases, ocular diseases associated with retinal vessel proliferation, Osier-Weber-Rendu disease, osteoarthritis, ovarian hyperstimulation syndrome, Paget's disease, pancreatitis, pemphigoid, polycystic kidney disease, polyps, postmenopausal osteoperosis, preeclampsia, psoriasis, pulmonary edema, pulmonary fibrosis, pulmonary sarcoidosis, restenosis, restenosis, retinopathy including diabetic retinopathy, retinopathy of prematurity and age related macular degeneration; rheumatoid arthritis, rheumatoid arthritis, rubeosis, sarcoidosis, sepsis, stroke, synovitis, systemic lupus erythematosus, throiditis, thrombic micoangiopathy syndromes, transplant rejection, trauma, tumor-associated angiogenesis, vascular graft restenosis, vascular graft restenosis, von Hippel Lindau disease, wound healing.

The present invention may be used in the treatment of macular dystrophy. This includes: Stargardt diseasefundus flavimaculatus; Stargardt-like macular dystrophy; Stargardt-like macular dystrophy; Autosomal dominant "bull'seye" macular dystrophy Best macular dystrophy; Adult vitelliform dystrophy; Pattern dystrophy; Doyne honeycomb retinal dystrophy; North Carolina macular dystrophy; Autosomal dominant macular dystrophy resembling MCDR1; North Carolina-like macular dystrophy associated with deafness; Progressive bifocal chorioretinal atrophy; Sorsby's fundus dystrophy; Central areolar choroidal dystrophy; Dominant cystoid macular dystrophy; Juvenile retinoschisis; Occult Macular Dystrophy; Non-familial Occult Macular Dystrophy.

The disorder may particularly be a disorder of the retinal epithelium, such as geographic atrophy, or age related macular degeneration.

For further details on of microvascular hyperpermeability disorders, disorders of epithelial cell survival and disorders of fenestrations of epithelial filtration membranes, and the treatment thereof, see WO 2010058227, the contents of which are incorporated herein by reference.

Neuropathic and Neurodegenerative Disorders

The compounds of the present invention, as SRPK1 inhibitors, may also be used as therapeutic agents in treating other disorders in which the alternatively spliced VEGF$_{xxx}$b isoform has been implicated. For example, it has been shown in WO 2009/106855, the contents of which are incorporated herein by reference, that VEGF$_{xxx}$b has neuroprotective and neuroregenerative effects.

Neuropathic disorders to be treated or prevented according to the present invention include neuropathic pain and diabetic and other neuropathies.

Neurodegenerative disorders to be treated or prevented according to the present invention include neurodegeneration of the cognitive and non-cognitive types, neuromuscular degeneration, motor-sensory neurodegeneration, ocular neurodegeneration.

The activities of the proteins of the VEGF$_{xxx}$b family are predicted to both actively prevent and actively reverse the conditions and disorders.

Furthermore, since mild cognitive dysfunction is often associated with the normal state in certain classes of healthy people, for example the aged, persons under stress, tired or exhausted persons, the present invention is also applicable to non-therapeutic treatments of healthy people to adjust or normalise their cognitive function and behaviour, including thinking, memory, learning, concentration and reasoning.

Still further, since neuroregeneration can assist in normalising brain neural networks in subjects having psychiatric or behavioural abnormalities, whether or not these are diagnosable as one or more recognised psychiatric condition, the present invention is also applicable to therapeutic treatment of persons having psychiatric disorders and to non-therapeutic treatment of physically healthy people to adjust their cognition and behaviour towards the normal state.

For example, the present invention provides for the treatment or prevention of: pain (for example, neuropathic pain), dementia, age-related cognitive impairment, Alzheimer's disease, senile dementia of the Alzheimer's type (SDAT), Lewy body dementia, vascular dementia, Parkinson's disease, postencephalitic Parkinsonism, depression, schizophrenia, muscular dystrophy including facioscapulohumeral muscular dystrophy (FSH), Duchenne muscular dystrophy, Becker muscular dystrophy and Bruce's muscular dystrophy, Fuchs' dystrophy, myotonic dystrophy, corneal dystrophy, reflex sympathetic dystrophy syndrome (RSDSA), neurovascular dystrophy, myasthenia gravis, Lambert Eaton disease, Huntington's disease, motor neurone diseases including amyotrophic lateral sclerosis (ALS), multiple sclerosis, postural hypotension, traumatic neuropathy or neurodegeneration e.g. following stroke or following an accident (for example, traumatic head injury or spinal cord injury), Batten's disease, Cockayne syndrome, Down syndrome, corticobasal ganglionic degeneration, multiple system atrophy, cerebral atrophy, olivopontocerebellar atrophy, dentatorubral atrophy, pallidoluysian atrophy, spinobulbar atrophy, optic neuritis, sclerosing pan-encephalitis (SSPE), attention deficit disorder, post-viral encephalitis, post-poliomyelitis syndrome, Fahr's syndrome, Joubert syndrome, Guillain-Barre syndrome, lissencephaly, Moyamoya disease, neuronal migration disorders, autistic syndrome, polyglutamine disease, Niemann-Pick disease, progressive multifocal leukoencephalopathy, pseudotumor cerebri, Refsum disease, Zellweger syndrome, supranuclear palsy, Friedreich's ataxia, spinocerebellar ataxia type 2, Rhett syndrome, Shy-Drager syndrome, tuberous sclerosis, Pick's disease, chronic fatigue syndrome, neuropathies including hereditary neuropathy, diabetic neuropathy and mitotic neuropathy, prion-based neurodegeneration, including Creutzfeldt-Jakob disease (CJD), variant CJD, new variant CJD, bovine spongiform encephalopathy (BSE), GSS, FFI, kuru and Alper's syndrome, Joseph's disease, acute disseminated encephalomyelitis, arachnoiditis, vascular lesions of the central nervous system, loss of extremity neuronal function, Charcot-Marie-Tooth disease, Krabbe's disease, leukodystrophies, susceptibility to heart failure, asthma, epilepsy, auditory neurodegeneration, macular degeneration, pigmentary retinitis and glaucoma-induced optic nerve degeneration.

Generally speaking, mental disorders are not diagnosed as "psychiatric disorders" unless the associated behaviours or thoughts cause significant distress to the individual or are disruptive of his or her everyday functioning. There is therefore a borderline between diagnosable disorders and similar, but less severe or disruptive, psychological functions the treatment of which should be considered as non-therapeutic (see below).

Examples of psychiatric disorders with which the present invention is concerned include, without limitation: anxiety disorders (for example, acute stress disorder, panic disorder, agoraphobia, social phobia, specific phobia, obsessive-compulsive disorder, sexual anxiety disorders, post-traumatic stress disorder, body dysmorphic disorder and generalized anxiety disorder), childhood disorders (for example, attention-deficit hyperactivity disorder (ADM)), Asperger's disorder, autistic disorder, conduct disorder, oppositional defiant disorder, separation anxiety disorder and Tourette's disorder), eating disorders (for example, anorexia nervosa and bulimia nervosa), mood disorders (for example, depression, major depressive disorder, bipolar disorder (manic depression), seasonal affective disorder (SAD), cyclothymic disorder and dysthymic disorder), sleeping disorders, cognitive psychiatric disorders (for example, delirium, amnestic disorders), personality disorders (for example, paranoid personality disorder, schizoid personality disorder, schizotypal personality disorder, antisocial personality disorder, borderline personality disorder, histrionic personality disorder, narcissistic personality disorder, avoidant personality disorder, dependent personality disorder and obsessive-compulsive personality disorder), psychotic disorders (for example, schizophrenia, delusional disorder, brief psychotic disorder, schizophreniform disorder, schizoaffective disorder and shared psychotic disorder), and substance-related disorders (for example, alcohol dependence, amphetamine dependence, cannabis dependence, cocaine dependence, hallucinogen dependence, inhalant dependence, nicotine dependence, opioid dependence, phencyclidine dependence and sedative dependence).

For further details on neuropathic and neurodegenerative disorders, and the treatment thereof, see WO 2009/106855, the contents of which are incorporated herein by reference.

Treatment of Pain

The compounds of the present invention, as SRPK1 inhibitors, may also be used as therapeutic agents in treating other disorders in which the alternatively spliced $VEGF_{xxx}b$ isoform has been implicated. For example, it has been shown in WO 2011148200, the contents of which are incorporated herein by reference, that $VEGF_{xxx}b$ has an analgesic effect on VEGFR2-mediated non-inflammatory pain in mammals.

VEGFR2-mediated non-inflammatory pain to be treated or prevented according to the present invention includes non-inflammatory neuropathic and nociceptive pain where the VEGFR2 receptor is involved in the cause or transmission of the pain. For example, the compounds according to the present invention have activity against non-inflammatory allodynia and pain (antiallodynic and analgesic activity). Pain states of this type include chronic pain, whether of the intermittent or constant form. Such pain states may include, for example, low back pain, neuralgia, atypical pains such as atypical facial pain, pain exhibited post-surgery, post-injury (for example, after surgery or injury causing nerve damage) or in association with cancer or with cancer therapy such as cytotoxic or radiation therapy, or neuropathy associated with diabetes (diabetic neuropathy, insulin neuritis) or other systemic or autoimmune disease or pathology, or the treatment thereof, alcoholism or HIV infection, ageing associated neuropathy, or neuropathy of unknown origin.

The activities of the proteins of the VEGFR2 agonists, for example the $VEGF_{xxx}b$ family, are predicted to both actively prevent and actively reverse VEGFR2-mediated non-inflammatory pain.

However, in view of the anti-angiogenic activity of the proteins of the $VEGF_{xxx}b$ family, use of the compounds of the present invention will be restricted to pain in contexts where possible inhibition of angiogenesis would not be detrimental to the patient. In view of the likely pro-angiogenic activity of full VEGFR2 agonists, use of full VEGFR2 agonists will be restricted to pain in contexts where possible stimulation of angiogenesis would not be detrimental to the patient.

The compounds used in the present invention may be employed in association with one or more different pain treatment agent for the purpose of normalising the sensitivity towards pain of the subject treated (or being co-treated) with the said one or more different pain treatment agent. The term "normalising" means moving the subject's pain sensitivity towards normal levels, and may include enhancement of the sensitivity if the one or more different pain treatment agent causes an excessive reduction in feeling or in sensitivity towards pain. The one or more different pain treatment agent may be selected from pain treatment agents currently known or yet to be devised. Such selection will be well within the skill of the person of ordinary skill in this art. Such combination treatments can enable fine control of pain sensitivity in subjects and minimisation of overall side effects according to the particular condition and needs of the subject.

For further details on pain, and the treatment thereof, see WO 2011/148200, the contents of which are incorporated herein by reference.

Reduction of Risk of Pre-Eclampsia

The compounds of the present invention, as SRPK1 inhibitors, may also be used as therapeutic agents in treating other disorders in which the alternatively spliced $VEGF_{xxx}b$ isoform has been implicated. For example, it has been shown in WO 2011/036429, the contents of which are incorporated herein by reference, that reduced $VEGF_{xxx}b$ levels in pregnant female mammals increase the risk of the female mammal developing pre-eclampsia. Thus, compounds of the present invention may be used to increase $VEGF_{xxx}b$ levels in a pregnant female mammal so as to reduce the risk of pre-eclampsia the female mammal developing pre-eclampsia or a complication linked thereto, or of a fetus of the female mammal developing a fetal or neonatal deficiency linked to maternal pre-eclampsia.

Pre-eclampsia in humans can develop as early as 20 weeks of gestation. Pre-eclampsia that develops before about 34 weeks of gestation is normally referred to as "early pre-eclampsia" or "early-onset pre-eclampsia". Pre-eclampsia that develops after about 34 weeks of gestation is normally referred to as "late pre-eclampsia" or "late-onset pre-eclampsia".

In addition, pre-eclampsia can be categorised as "severe pre-eclampsia" according to criteria established by the United Kingdom Royal College of Obstetricians and Gynaecologists. Under these criteria, a patient with "severe pre-eclampsia" will have systolic blood pressure (BP) greater than 169 mmHg or diastolic BP greater than 109 mmHg with proteinuria greater than 1 g/24 h; or will show occurrence of HELLP syndrome (haemolysis, elevated liver enzymes and low platelet count).

For further details on pre-eclampsia, and methods to reduce the risk of a pregnant female mammal developing developing pre-eclampsia or a complication linked thereto, or of a fetus of the female mammal developing a fetal or neonatal deficiency linked to maternal pre-eclampsia, see WO 2011/036429, the contest of which are incorporated herein by reference.

Active Compounds

Compounds of the present invention are as defined by Formula (I) and have been shown to be inhibitors of one or both of the kinases SRPK1, and SRPK2, and thus useful in treatments as described herein.

WO 2005/063293, incorporated herein by reference in its entirety, with particular reference to the explicitly exemplified compounds and preferred positions, describes known SRPK inhibitor SRPIN-1 (also referred to herein as SRPIN340) and its analogues as anti-viral agents.

The compounds of the present invention may be synthesised by any known method. Suitable methods as disclosed in WO 2005/063293 may be adapted as required.

Co-Administration

The compounds of the present invention may, if desired, be co-administered with one or more additional active agent, for example one or more agent selected from, but not limited to, cholinesterase inhibitors, dopamine agonists (e.g. L-dopa), COMT inhibitors, MAO-B inhibitors, anti-cholinergics, acetylcholine agonists, serotonin agonists, AMPA receptor agonists, GABA receptor agonists, NMDA receptor agonists, β-adrenoceptor agonists, digoxin, dobutamine, anti-inflammatories, neurotrophic factors, statins, adenosine A2a receptor antagonists, aldose reductase inhibitors, immunomodulators, cannabinoid agonists, interferon or tricyclic anti-depressants.

Definitions

In the definition of formula (I) herein:

"$C_{1-6}$ alkyl group" refers to a linear or branched alkyl group comprising one to six carbon atoms, which is a monovalent group derived by removing an arbitrary hydrogen atom from an aliphatic hydrocarbon consisting of one to six carbons. Specifically, the $C_{1-6}$ alkyl group includes, for example, a methyl group, an ethyl group, a 1-propyl group, a 2-propyl group, a 2-methyl-1-propyl group, a 2-methyl-2-propyl group, a 1-butyl group, a 2-butyl group, a 1-pentyl group, a 2-pentyl group, a 3-pentyl group, a 2-methyl-1-butyl group, a 3-methyl-1-butyl group, a 2-methyl-2-butyl group, a 3-methyl-2-butyl group, a 2,2-dimethyl-1-propyl group, a 1-hexyl group, a 2-hexyl group, a 3-hexyl group, a 2-methyl-1-pentyl group, a 3-methyl-1-pentyl group, a 4-methyl-1-pentyl group, a 2-methyl-2-pentyl group, a 3-methyl-2-pentyl group, a 4-methyl-2-pentyl group, a 2-methyl-3-pentyl group, a 3-methyl-3-pentyl group, a 2,3-dimethyl-1-butyl group, a 3,3-dimethyl-1-butyl group, a 2,2-dimethyl-1-butyl group, a 2-ethyl-1-butyl group, a 3,3-dimethyl-2-butyl group, and a 2,3-dimethyl-2-butyl group;

"$C_{2-6}$ alkenyl group" refers to a linear or branched alkenyl group comprising two to six carbons. Specifically, the $C_{2-6}$ alkenyl group includes, for example, a vinyl group, an allyl group, a 1-propenyl group, a 2-propenyl group, a 1-butenyl group, a 2-butenyl group, a 3-butenyl group, a pentenyl group, and a hexenyl group;

"$C_{2-6}$ alkynyl group" refers to a linear or branched alkynyl group comprising two to six carbons. Specifically, the $C_{2-6}$ alkynyl group includes, for example, an ethynyl group, a 1-propynyl group, a 2-propynyl group, a butynyl group, a pentynyl group, and a hexynyl group.

"$C_{1-6}$ alkoxy group" refers to an oxy group to which the above-defined "$C_{1-6}$ alkyl group" is linked. Specifically, the $C_{1-6}$ alkoxy group includes, for example, a methoxy group, an ethoxy group, a 1-propyloxy group, a 2-propyloxy group, a 2-methyl-1-propyloxy group, a 2-methyl-2-propyloxy group, a 1-butyloxy group, a 2-butyloxy group, a 1-pentyloxy group, a 2-pentyloxy group, a 3-pentyloxy group, a 2-methyl-1-butyloxy group, a 3-methyl-1-butyloxy group, a 2-methyl-2-butyloxy group, a 3-methyl-2-butyloxy group, a 2,2-dimethyl-1-propyloxy group, a 1-hexyloxy group, a 2-hexyloxy group, a 3-hexyloxy group, a 2-methyl-1-pentyloxy group, a 3-methyl-1-pentyloxy group, a 4-methyl-1-pentyloxy group, a 2-methyl-2-pentyloxy group, a 3-methyl-2-pentyloxy group, a 4-methyl-2-pentyloxy group, a 2-methyl-3-pentyloxy group, a 3-methyl-3-pentyloxy group, a 2,3-dimethyl-1-butyloxy group, a 3,3-dimethyl-1-butyloxy group, a 2,2-dimethyl-1-butyloxy group, a 2-ethyl-1-butyloxy group, a 3,3-dimethyl-2-butyloxy group, and a 2,3-dimethyl-2-butyloxy group;

"$C_{1-6}$ alkylthio group" refers to a thio group to which the above-defined "$C_{1-6}$ alkyl group" is linked. Specifically, the "$C_{1-6}$ alkylthio group" includes, for example, a methylthio group, an ethylthio group, a 1-propylthio group, a 2-propylthio group, a butylthio group, and a pentylthio group;

"$C_{1-6}$ alkoxycarbonyl group" refers to a carbonyl group to which the above-defined "$C_{1-6}$ alkoxy group" is linked. Specifically, the $C_{1-6}$ alkoxycarbonyl group includes, for example, a methoxy carbonyl group, an ethoxy carbonyl group, a 1-propyloxycarbonyl group, and a 2-propyloxycarbonyl group;

"$C_{1-6}$ alkylsulfonyl group" refers to a sulfonyl group to which the above-defined "$C_{1-6}$ alkyl group" is linked. Specifically, the $C_{1-6}$ alkylsulfonyl group includes, for example, a methylsulfonyl group, an ethylsulfonyl group, a 1-propylsulfonyl group, and a 2-propylsulfonyl group.

"halogen atom" refers to a fluorine atom, a chlorine atom, a bromine atom, or an iodine atom;

"$C_{6-10}$ aryl group" refers to an aromatic cyclic hydrocarbon group comprising six to ten carbon atoms. Specifically, the $C_{6-10}$ aryl group includes, for example, a phenyl group, a 1-naphthyl group, and a 2-naphthyl group;

"heterocycle" refers to an aromatic or non-aromatic ring that may comprise double bonds within the ring, wherein at least one, for example one or two, of the atoms constituting the ring are heteroatoms;

"nitrogen-containing heterocycle" refers to an aromatic or non-aromatic ring that may comprise double bonds within the ring, wherein at least one, for example one or two, of the atoms constituting the ring are nitrogen atoms;

"oxygen-containing heterocycle" refers to an aromatic or non-aromatic ring that may comprise double bonds within the ring, wherein at least one, for example one or two, of the atoms constituting the ring are oxygen atoms;

"heteroatom" refers to a sulfur atom, an oxygen atom, or a nitrogen atom;

"nitrogen-containing 5- to 10-membered heteroaryl ring" refers to an aromatic ring in which five to ten atoms constitute the ring, wherein at least one of the atoms constituting the ring is a nitrogen atom, and one or more heteroatoms other than nitrogen atoms may further be comprised. Specifically, the nitrogen-containing 5- to 10-membered heteroaryl ring includes, for example, a pyridine ring, a pyrrole ring, an oxazole ring, an isoxazole ring, a thiazole ring, an isothiazole ring, an indole ring, an isoindole ring, an imidazole ring, a triazole ring, a pyrazole ring, a pyridazine ring, a pyrimidine ring, a pyrazine ring, a quinoline ring, an isoquinoline ring, and a benzimidazole ring. The "5- to 10-membered heteroaryl ring" preferably includes a pyridine ring, a pyrrole ring, and an imidazole ring, and more preferably includes a pyridine ring;

"Nitrogen-containing 5- and 10-membered heteroaryl group" refers to a mono- or divalent group derived by removing one or two arbitrary hydrogen atoms from the above-defined "5- and 10-membered heteroaryl ring". Specifically, the nitrogen-containing 5- and 10-membered heteroaryl group includes, for example, a pyridyl group, a pyrrolyl group, an oxazolyl group, an isoxazolyl group, a thiazolyl group, an isothiazolyl group, an indolyl group, an isoindolyl group, an imidazolyl group, a triazolyl group, a pyrazolyl group, a pyridazinyl group, a pyrimidinyl group, a pyrazinyl group, a quinolyl group, an isoquinolyl group, and a benzimidazolyl group;

"Oxygen-containing 5- to 10-membered heteroaryl ring" refers to an aromatic ring in which five to ten atoms constitute the ring, wherein at least one of the atoms constituting the ring is an oxygen atom, and one or more heteroatoms other than oxygen atoms may further be comprised;

"4- to 8-membered heterocyclic ring" refers to anon-aromatic ring that meets the following definition:
1. four to eight atoms constitute the ring;
2. one or two of the atoms constituting the ring are heteroatoms;
3. one or two double bonds may be comprised in the ring;
4. one to three carbonyl groups may be comprised in the ring; and
5. the group is monocyclic.

The 4- to 8-membered heterocyclic ring is preferably a nitrogen-containing 4- to 8-membered heterocyclic ring that comprises nitrogen atoms as heteroatoms.

Specifically, the 4- to 8-membered heterocyclic ring includes, for example, an azetidine ring, a pyrrolidine ring, a piperidine ring, an azepane ring, an azocine ring, a furan ring, a tetrahydropyran ring, a morpholine ring, a thiomorpholine ring, a piperazine ring, a thiazolidine ring, a dioxane ring, an imidazoline ring, and a thiazoline ring. The "4- to 8-membered heterocyclic ring" preferably includes a pyrrolidine ring, a piperidine ring, a morpholine ring, and a piperazine ring;

"A 4- to 8-membered heterocyclic group" refers to a mono- or divalent group derived by removing one or two arbitrary hydrogen atoms from the above-defined "4- to 8-membered heterocyclic ring". Specifically, the 4- to 8-membered heterocyclic group includes, for example, an azetidinyl group, a pyrrolidinyl group, a piperidinyl group, an azepanyl group, an azocanyl group, a furyl group, a tetrahydropyranyl group, a morpholinyl group, a thiomorpholinyl group, a piperazinyl group, a thiazolidinyl group, a dioxanyl group, an imidazolyl group, and a thiazolyl group;

"Condensed aromatic heterocycle" refers to a ring structure in which the heterocyclic moiety is fused, for example ortho-condensed, with an aromatic ring, such as a benzene ring. The heterocyclic moiety is an above-defined heterocycle.

"Condensed aromatic heterocyclic group" refers to a ring structure in which the heterocyclic moiety is fused, for example ortho-condensed, with an aromatic ring, such as benzene ring. The heterocyclic moiety is an above-defined heterocyclic group.

The condensed aromatic heterocyclic group includes, for example, an indolinyl group, an isoindolinyl group, and a 1,2,3,4-tetrahydroquinoline.

Herein, "halogenated $C_{1-6}$ alkyl group" refers to a group in which at least one arbitrary hydrogen atom in the above-defined "$C_{1-6}$ alkyl group" is replaced with an above-defined "halogen atom". The halogenated $C_{1-6}$ alkyl group includes, for example, a trifluoromethyl group, a difluoromethyl group, and a monofluoromethyl group.

Herein, the phrase "may have one or more substituent" means that a certain group or compound may optionally have an arbitrary selection or combination of one or more substituent at substitutable positions. Specifically, the substituents can include, for example, atoms or groups selected from one or more of: halogen, hydroxyl, mercapto, nitro, cyano, formyl, carboxyl, trifluoromethyl, trifluoromethoxy, amino, oxo, imino, $C_{1-6}$ alkyl (for example methyl), $C_{1-6}$ alkoxy (for example, methoxy), heteroaryl, phenyl, or phenyl or heteroaryl substituted by one or more of halogen, hydroxyl, mercapto, nitro, cyano, formyl, carboxyl, trifluoromethyl, trifluoromethoxy, amino, oxo, imino, $C_{1-6}$ alkyl (for example methyl) or $C_{1-6}$ alkoxy (for example, methoxy).

"Salt" is not particularly limited, so long as it is a pharmaceutical acceptable salt which is formed with a compound according to the present invention. Such salts include, for example, inorganic acid salts, organic salts, inorganic base salts, organic base salts, and acidic or basic amino acid salts. Examples of preferable inorganic acid salts include: hydrochloride, hydrobromate, sulfate, nitrate, and phosphate. Examples of preferable organic salts include:

acetate, succinate, fumarate, maleate, tartrate, citrate, lactate, stearate, benzoate, methanesulfonate, and p-toluene sulfonate.

Examples of preferable inorganic base salts include: alkali metal salts, such as sodium salts and potassium salts; alkali earth metal salts, such as calcium salts and magnesium salts; aluminium salts; and ammonium salts. Examples, of preferable organic base salts include: diethylamine salts, diethanol amine salts, meglumine salts, and N,N'-dibenzylethylenediamine salts.

Examples of preferable acidic amino acid salts include: aspartate and glutamate. Examples of preferable basic amino acid salts include: arginine salts, lysine salts, and ornithine salts.

When left in air, the compounds of the present invention sometimes absorb moisture, and are sometimes attached to absorbed water or converted to hydrates. Such hydrates are also included in the present invention.

Furthermore, compounds of the present invention are sometimes converted into solvates, absorbing some other solvents. Such solvates are also included in the present invention.

Any organic solvent may in principle be used to prepare a solvate of the compounds of the present invention.

A solvate can include also water together with the one or more organic solvent.

Thus, for example, the solvent may be selected from ketones, alcohols, ethers, esters, aromatic solvents, and, where possible, mixtures thereof with each other, with other organic solvents and/or with water.

Pharmaceutically acceptable prodrug forms of the compounds of formula (I) may be used in the present invention. "Pharmaceutically acceptable prodrugs" means those prodrugs of the compounds which are, within the scope of sound medical and vetinary judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds. The term "prodrug" means compounds that are rapidly transformed in vivo to yield the parent compound of the above formula, for example by hydrolysis in blood. Functional groups which may be rapidly transformed, by metabolic cleavage, in vivo form a class of groups reactive with the carboxyl group. Because of the ease with which the metabolically cleavable groups of the compounds are cleaved in vivo, the compounds bearing such groups act as pro-drugs. A thorough discussion of prodrugs is provided in the following: Design of Prodrugs, H. Bundgaard, ed., Elsevier, 1985; Methods in Enzymology, K. Widder et al, Ed., Academic Press, 42, p. 309-396, 1985; A Textbook of Drug Design and Development, Krogsgaard-Larsen and H. Bundgaard, ed., Chapter 5; Design and Applications of Prodrugs p. 113-191, 1991; Advanced Drug Delivery Reviews, H. Bundgard, 8, p. 1-38, 1992; Journal of Pharmaceutical Sciences, 77, p. 285, 1988; Chem. Pharm. Bull., N. Nakeya et al, 32, p. 692, 1984; Pro-drugs as Novel Delivery Systems, T. Higuchi and V. Stella, Vol. 14 of the A. C. S. Symposium Series, and Bioreversible Carriers in Drug Design, Edward B. Roche, ed., American Pharmaceutical Association and Pergamon Press, 1987, which are incorporated herein by reference.

Compositions and Administration

The compound according to the present invention may be administered in the form of a composition comprising the active agent and any suitable additional component. The composition may, for example, be a pharmaceutical composition (medicament), suitably for topical administration (e.g. as eyedrops or cream or lotion), or parenteral administration (e.g. injection, implantation or infusion). The composition may alternatively, for example, be a foodstuff, food supplement, beverage or beverage supplement.

The term "pharmaceutical composition" or "medicament" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may take the form, for example, of tablets, dragees, powders, elixirs, syrups, liquid preparations including suspensions, sprays, inhalants, tablets, lozenges, emulsions, solutions, cachets, granules, capsules and suppositories, as well as liquid preparations for injections, including liposome preparations. Techniques and formulations generally may be found in Remington, The Science and Practice of Pharmacy, Mack Publishing Co., Easton, Pa., latest edition.

Liquid form preparations include solutions, suspensions, and emulsions. As an example may be mentioned water or water-propylene glycol solutions for parenteral injection or topical administration. Liquid preparations can also be formulated in solution in aqueous polyethylene glycol solution.

Also included are solid form preparations which are intended to be converted, shortly before use, to liquid form preparations for either topical, oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container or apparatus. The solid form preparations intended to be converted to liquid form may contain, in addition to the active material, flavourings, colourants, stabilizers, buffers, artificial and natural sweeteners, dispersants, thickeners, solubilising agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for topical or parenteral use.

The composition may be in a formulation intended for topical application. The formulation may be a gelling formulation to control release and therefore availability of the active agent following topical application. The formulation may contain one or more gelling agents, for example hydroxypropyl methylcellulose. The formulation may contain one or more surfactants, for example a non-ionic liquid polymer, examples of which include Tyloxapol, and the Pluronics® poloxamers from BASF. The formulation may contain one or more solubilizers, for example dextrose or sorbitol. The formulation may contain one or more antimicrobial or antiseptic agents, for example benzalkonium chloride. The aforementioned named gelling agents, surfactants, solubilizers and antimicrobial agents are listed purely by way of example and it will be appreciated that other agents to perform these functions are known.

The dosages may be varied depending upon the requirements of the patient, the severity of the condition being treated, and the compound being employed. Determination of the proper dosage for a particular situation is within the skill of the art. Generally, treatment is initiated with the smaller dosages which are less than the optimum dose of the compound. Thereafter the dosage is increased by small increments until the optimum effect under the circumstances is reached. For convenience, the total daily dosage may be divided and administered in portions during the day if desired.

The dosage regime for administration of the active agent may, for example, comprise a total dose of up to 1 µg, for example up to 500 ng, for example up to 50 ng, for example less than 20 ng of active agent in a dosing period ranging, for example, between 1 and 14 days. For example, a total dose of less than 18 ng, 17 ng, 16 ng, 15, ng, 14 ng, 13 ng, 12 ng, 11 ng or 10 ng may be administered.

The compound of Formula (I) or a pharmaceutically acceptable salt, solvate, hydrate or prodrug thereof may be administered in a therapeutically effective amount. A therapeutically effective amount of a compound of Formula (I) for topical administration for treatment of CNV may be at least about 5 µg10 µl of delivery vehicle. Alternatively, a therapeutically effective amount may be at least about 100 µg/mL, for example at least about 200 µg/mL, at least about 300 µg/mL, at least about 400 µg/mL, at least about 500 µg/mL, at least about 600 µg/mL, at least about 700 µg/mL, at least about 800 µg/mL, at least about 900 µg/mL, or at least about 1000 µg/mL, Alternatively, a therapeutically effective amount may be at least about 1 mg/mL, for example at least about 2 mg/mL, at least about 3 mg/mL, at least about 4 mg/mL, at least about 5 mg/mL. Alternatively, a therapeutically effective amount may be less than about 5 mg/mL, for example less than about 4 mg/mL, less than about 3 mg/mL, less than about 2 mg/mL, less than about 1 mg/mL. The therapeutically effective amount may be administered daily, for a dosing period ranging, for example, between 1 and 14 days. The therapeutically effective amount may be a total daily dosage which may be divided and administered in portions during the day, for example twice daily.

A therapeutically effective amount of a compound of Formula (I) for anti-angiogenic treatment of a mammalian subject, or for use in treating or preventing microvascular hyperpermeability disorders, or in regulating the pro-angiogenic pro-permeability properties of $VEGF_{xxx}$ isoforms, or in supporting epithelial cell survival without increased permeability, or in reducing the nature (for example the number density and/or size) of fenestrations of epithelial filtration membranes, or for use in treating or preventing neuropathic and neurodegenerative disorders, or for use as a neuroprotective or neuroregenerative agent in vivo or in vitro, or for use in treating or preventing VEGFR2-mediated non-inflammatory pain, or for use in reducing the risk of a female mammal developing pre-eclampsia or a complication linked thereto, or of a fetus of the female mammal developing a fetal or neonatal deficiency linked to maternal pre-eclampsia may be calculated according to body mass of the subject to be treated, and may be at least about 20 mg/kg, for example at least about 30 mg/kg, at least about 40 mg/kg, at least about 50 mg/kg, at least about 60 mg/kg, at least about 70 mg/kg, at least about 80 mg/kg, at least about 90 mg/kg, at least about 100 mg/kg. Alternatively, the therapeutically effective amount may be less than about 100 mg/kg, for example less than about 90 mg/kg, less than about 80 mg/kg, less than about 70 mg/kg, less than about 60 mg/kg, less than about 50 mg/kg, less than about 40 mg/kg, less than about 30 mg/kg, or less than about 20 mg/kg, for example less than about 10 mg/kg, less than about 5 mg/kg.

"Treating or Preventing"

The expression "treating or preventing" and analogous terms used herein refers to all forms of healthcare intended to remove or avoid the disorder or to relieve its symptoms, including preventive, curative and palliative care, as judged according to any of the tests available according to the prevailing medical and psychiatric practice. An intervention that aims with reasonable expectation to achieve a particular result but does not always do so is included within the expression "treating or preventing". An intervention that succeeds in slowing or halting progression of a disorder is included within the expression "treating or preventing".

Certain neurological and psychiatric disorders are considered as "spectrum" conditions, in which individuals may exhibit some or all of a range of possible symptoms, or may exhibit only a mild form of the disorder. Furthermore, many neurological and psychiatric conditions are progressive, starting with relatively mildly abnormal symptoms and progressing to more severely abnormal symptoms. The present invention includes the treatment and prevention of all neurological and psychiatric conditions of whatever type and stage.

"Susceptible to"

The expression "susceptible to" and analogous terms used herein refers particularly to individuals at a higher than normal risk of developing a medical or psychiatric disorder, or a personality change, as assessed using the known risk factors for the individual or disorder. Such individuals may, for example, be categorised as having a substantial risk of developing one or more particular disorders or personality changes, to the extent that medication would be prescribed and/or special dietary, lifestyle or similar recommendations would be made to that individual.

"Non-Therapeutic Method"

The expression "non-therapeutic method" used herein refers particularly to an intervention performed on an individual who is neurologically or psychologically within the normal range, to normalise or enhance or improve a function of the neurological or psychological kind. A neurological function that may suitably be treated non-therapeutically may include, for example, cognition (including thinking, reasoning, memory, recall, imagining and learning), concentration and attention, particularly towards the milder end of the scale of conditions, and mild abnormal behavioural or personality traits. A psychological function that may suitably be treated non-therapeutically may include, for example, human behaviour, mood, personality and social function, for example grief, anxiety, depression, moodiness, moroseness, teenage moods, disrupted sleep patterns, vivid dreaming, nightmares, and sleepwalking.

There is a borderline between diagnosable neurological and psychiatric disorders and (non-diagnosable) neurological and psychological functions within the normal range. Therefore, in addition to the examples of neurological and psychological functions give above that are treatable according to the non-therapeutic methods of the present invention, mild forms of neurological and psychiatric disorders, that are non-diagnosable because the associated behaviours or thoughts do not cause significant distress to the individual or are not disruptive of his or her everyday functioning, are also to be considered as conditions treatable non-therapeutically according to the present invention.

"Normalise"

The expression "normalise" and analogous terms used herein refers particularly to a physiological adjustment towards a condition characteristic of general normal neurological or psychiatric health, whether or not a condition is actually reached that would be characterised as normal.

Mammals

Besides being useful for human treatment, the present invention is also useful in a range of mammals. Such mammals include non-human primates (e.g. apes, monkeys and lemurs), for example in zoos, companion animals such as cats or dogs, working and sporting animals such as dogs, horses and ponies, farm animals, for example pigs, sheep, goats, deer, oxen and cattle, and laboratory animals such as rodents (e.g. rabbits, rats, mice, hamsters, gerbils or guinea pigs).

Where the disorder or function to be treated is exclusive to humans, then it will be understood that the mammal to be treated is a human. The same applies respectively to any other mammalian species if the disorder or function to be treated is exclusive to that species.

BRIEF DESCRIPTION OF THE DRAWINGS

Embodiments of the present invention will now be described, purely by way of example, and with reference to the accompanying drawings, in which.

METHODS

Cell culture

Figure 1:
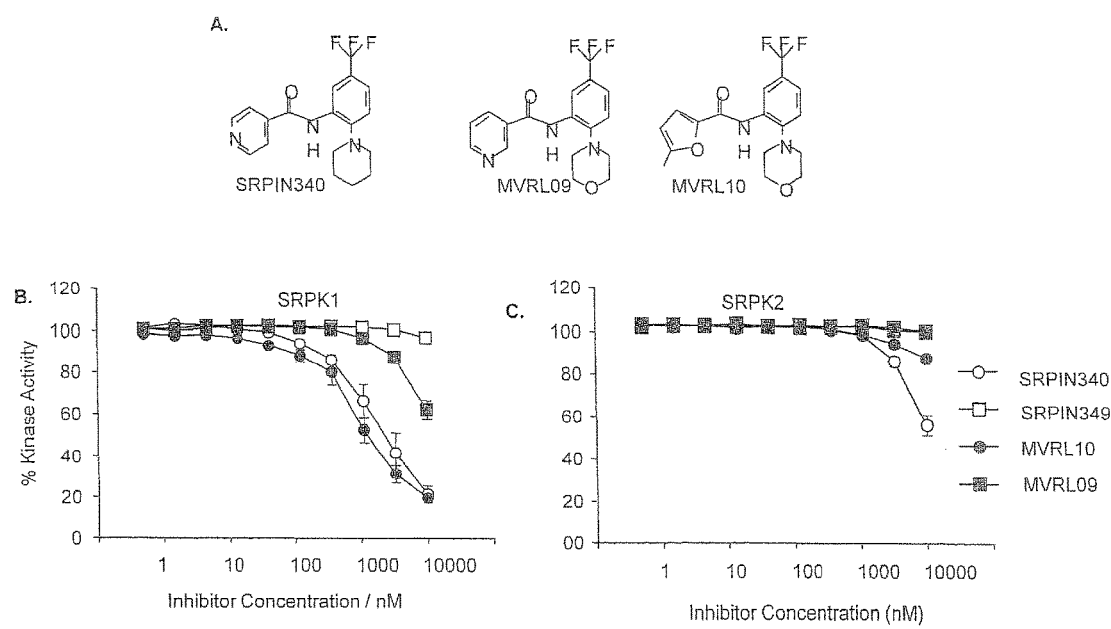
FIG. 1A shows the structures of three compounds which exhibit activity against SRPK1 and SRPK2.
FIGS. 1B and 1C show the activity of the compounds of FIG. 1A against SRPK1 and SRPK2 respectively.

Primary human RPE isolations were performed on human donor globes obtained within 24 hours post-mortem from the Bristol Eye bank (Bristol Eye Hospital (BEH)). Retinas with choroid-RPE sheets were removed to a petri dish, finely chopped and digested in Dulbecco's Modified Eagle Medium (DMEM):F12(1:1)+GlutaMax (Gibco) supplemented with 0.3 mg/ml collagenase for 15 minutes at 37° C. Digested choroid-RPE sheets were suspended in media (DMEM:F12+GlutaMax) supplemented with 10% fetal bovine serum (FBS), 0.5% PenStrep (Invitrogen) and spun at 1500 rpm (251 g) for 10 minutes to pellet cells. Pellets were resuspended in media supplemented with 25% FBS (Gibco), grown in cell culture flasks (Greiner) and split at 80% confluence. ARPE-19 (ATCC) cells were cultured in DMEM:F12 plus 10% FBS, split at 80% confluence.

In Vitro Kinase Assay

Candidate compounds including MVRL09, MVRL10 (SPHINX), MVRL16 (SPHINX6), MVRL17 (SPHINX7), SPHINX8, SPHINX9, SPHINX10, SPHINX12, SPHINX13, SPHINX14 and SRPIN340 were screened by the Kinase-Glo assay (Promega; Koresawa and Okabe, 2004), the results of which are shown in Table 1. A reaction buffer containing 9.6 mM MOPS pH7 and 0.2 nM EDTA pH8 was added to 10 μM SRSF1 RS peptide (NH$_2$-RSPSYGRSRSRSKSRSRSRSRSNSRSRSY-OH (SEQ NO: 1)) and 0.1 μg of purified SRPK1 kinase. Candidate compounds were serially diluted from 10 μM-0.5 nM and added to the reaction mixture, wells with omitted SRPK1 kinase and omitted compounds were also added as controls. All wells contained one percent DMSO. One micromolar ATP was added, wells minus ATP were used as background controls. The plate was then incubated at 30° C. for 10 minutes. An equal volume of Kinase-Glo (Promega, 25 μl) was added to each well and the plate read for luminescence using an ARVO 5× (Perkin Elmer).

Pharmacological inhibitor treatments—SRPIN340, MVRL09 and MVRL10

SR protein phosphorylation inhibitors, SRPIN340 (N-[2-(1-piperidinyl)-5-(trifluoromethyl)phenyl]isonicotinamide; Ascent Scientific, Cambridge), MVRL09 (N-[2-(morpholin-4-yl)-5-(trifluoromethyl)phenyl]pyridine-3-carboxamide), MVRL10 (5-methyl-N-[2-(morpholin-4-yl)-5-(trifluoromethyl)phenyl]furan-2-carb-oxamide) were used. Cells at ~60% confluence were serum starved for at least 12 hours and treated with five or 10 μM compound inhibitors. Twenty-four hours later mRNA was extracted and 48 hours later protein was extracted, for further analyses.

Semi-Quantitative: Reverse Transcriptase (RT)-PCR for VEGF

Conventional PCR was used to detect $VEGF_{165}$ and $VEGF_{165}b$ mRNA. Five-ten percent of the cDNA was added to a reaction mixture containing: 2×PCR Master Mix (Promega), primers (1 μM each) complementary to exon7b (5'-GGC AGC TTG AGT TAA ACG AAC-3' (SEQ ID NO: 2)) and the 3'UTR of exon8b (5'-ATG GAT CCG TAT CAG TCT TTC CTG G-3' (SEQ ID NO: 3)) and DNase/RNase free water. All samples were run in parallel with negative controls (water and cDNA without reverse transcriptase (-RT)) and positive controls ($VEGF_{165}$ in a plasmid expression vector (pcDNA) and $VEGF_{165}b$ pcDNA). The reaction mixture was thermo cycled (PCR Express, Thermo Electron Corporation, Basingstoke) 30-35 times, denaturing at 95° C. for 60 seconds, annealing at 55° C. for 60 seconds and extending at 72° C. for 60 seconds. PCR products were separated on 2.5% agarose gels containing 0.5 μg/ml ethidium bromide (BioRad) and visualized under an ultra-violet transilluminator (BioRad).

Equal cDNA loading was determined by PCR with GAPDH primers (Forward: 5'-CAC CCA CTC CTC CAC CTT TGA C-3' (SEQ ID NO: 4); Reverse: 5'-GTC CAC CAC CCT GTT GCT GTA G-3' (SEQ ID NO: 5)). Primers result in one amplicon at ~112 bp after thermo cycling 30 times, denaturing at 94° C. for 45 seconds, annealing at 65° C. for 45 seconds and extending at 72° C. for 60 seconds.

PanVEGF and $VEGF_{xxx}b$ enzyme-linked immunosorbent assay (ELISA).

One μg/ml pan-VEGF capture antibody (Duoset VEGF ELISA DY-293; R&D systems) was incubated overnight at room temperature. The plates were blocked (Superblock; Thermo Scientific) and serial dilutions of recombinant human (rh)$VEGF_{165}$ or $rhVEGF_{165}b$ standards (ranging from 4 ng/ml to 16.25 pg/ml) were added, incubated alongside sample lysates, typically diluted 1:10. The plate was incubated for one hour at 37° C. with shaking, washed and incubated with 100 μl/well of either biotinylated goat anti-human VEGF (0.1 μg/ml; R & D systems) or mouse anti-human $VEGF_{165}b$ (0.25 μg/ml) for one further hour at 37° C. After washing, 100 μl/well of Horseradish Peroxidase (HRP)-conjugated streptavidin (1:200; R&D Systems) was added, and plates were left at room temperature for 20 minutes.

The plates were washed and colour change induced with substrate A and B (DY-999; R&D Systems) for 20 mins under light protection. The reaction was stopped by addition of 100 μl/well of 1M $H_2SO_4$ and the absorbance was read immediately in an ELISA plate reader (Dynex Technologies Opsys MR system plate reader) at 450 nm with a control reading at 570 nm. Revelation Quicklink 4.25 software was also used to calculate a standard curve from mean absorbance values of standards enabling the estimation of VEGF concentration for each sample.

Western Blotting

Protein samples (30-50 μg) were mixed with 1× sodium-dodecyl sulphate (SDS) loading buffer (100 mM Tris-HCl, 4% SDS, 20% glycerol, 0.2% (w/v) bromophenol blue, and 5% final concentration 2-mercaptoethanol, pH6.8). To denature the protein, samples were boiled for five minutes at 100° C.

Samples were subjected to polyacrylamide gel electrophoresis (PAGE) on a 12% SDS-PAGE gel at 90V in ice cold running buffer (25 mM Tris-HCl, 250 mM glycine, 0.1% SDS, pH8.3) for approximately 2.5 hours. The separated proteins were then electrophoretically blotted to a methanol-activated polyvinylidene fluoride (PVDF) membrane (Fisher Scientific) by wet transfer for two hours at 90V in transfer buffer (50 mM Tris-HCl, 38 mM glycine, 20% methanol, pH8.3). Membranes were incubated in blocking solution (2.5% non-fat dried milk in PBS/T or 5% BSA) with agitation at room temperature for 30 minutes, and then probed with the primary antibody overnight at 4° C.; rabbit polyclonal anti-VEGF-A (A20; sc-152, Santa Cruz) diluted 1:1000-1:200 in 2.5% non-fat dried milk PBS/T, $VEGF_{xxx}b$ specific mouse monoclonal 56/1 (R&D Systems) diluted 1:1000 in 5% BSA PBS/T, mouse monoclonal SRSF1 (SF2/ASF) (96; sc-33652, Santa Cruz) diluted 1:1000 in 2.5% non-fat dried milk PBS/T and mouse monoclonal anti-SRPK1 (BD Biosciences, 611072) diluted 1:1000 in 5% BSA PBS/T. Membranes were then washed four times for 10 minutes each with TBS/0.3% T before incubation with secondary HRP-conjugated antibodies: goatαmouse immunoglobulin G (IgG), goatαrabbit IgG or rabbitαgoat IgG (Pierce) diluted 1:10000 in 5% BSA PBS/T or 2.5% non-fat dried milk PBS/T, for 45 minutes at room temperature with agitation. The washes were repeated and the bands were detected using the Enhanced Chemoluminiscence (ECL) SuperSignal West Femto Maximum Sensitivity Substrate kit (Pierce).

Pharmacological Inhibitor Treatments—SPHINX6 and SPHINX7

Primary human RPE cells were treated with increasing concentrations of SPHINX for 24 hours as described (Gammons et al *Invest. Ophthalmol. Vis. Sci.* 54(9) 6052-6062), followed by RNA extraction, and RT-PCR carried out using primers that detect $VEGF_{165}$ (200 bp) or $VEGF_{165}b$ (130 bp) as previously described (Bates et al 2002). Cells were treated with SPHINX6 and 7 and the PCR repeated.

Protein was extracted from RPE cells treated for 48 hours with SPHINXes and subjected to western blotting for $VEGF_{165}b$ using anti-$VEGF_{165}b$ antibody as previously described (Gammons et al *Invest. Ophthahnol. Vis. Sci.* 54(9) 6052-6062).

Inhibition of SRSF1 Phosphorylation Induced by EGF Activation.

PC3 prostate cancer cells were treated with 10 nM EGF in the presence of either DMSO (Vehicle), SPHINX, SRPIN340 or SPHINX7 at 10 μM for 1 hr. Cells were lysed, and subjected to immunoblotting using an antibody to phosphorylated SR proteins (MAB104) and an antibody to tubulin as a loading control. Intensity was measured for SRSF1 and SRSF5 bands using ImageJ Intensity. Phosphorylation is calculated as the increase in intensity of the band over untreated relative to that for EGF with vehicle.

Laser Lesion Induction Protocol

Six to eight week-old C57/B6 mice (B&K Laboratories) and adult Norway-Brown rats (Harlan Laboratories) were anaesthetized with an intraperitoneal injection of a mixture of 50 mg/kg ketamine and 0.5 mg/kg medetomidine. The pupils were dilated with 2.5% phenylephrine hydrochloride and 1% tropicamide. Four photocoagulation lesions were delivered with a krypton red laser (Mice: 250 mW, 0.01 s, 75 μm, Rats: 200 mW, 0.01 s, 75 μm, IRIS Medical 810 nm Oculight Slx laser) between the retinal vessels in a peripapillary distribution at a distance of 1-2 disc-diameters in each eye. Only laser lesions with a subretinal bubble at the time of treatment were included in the study. Immediately following laser photocoagulation the animals either received intravitreal injections in both eyes (day 0 and day 7), or given topical eye drops twice daily of 100 μg mL SRPIN340 or different doses of SPHINX7 (10 µl volumes) in one eye and control vehicle in the other eye. Animals were culled on either day 4 or day 14 and eyes were either unfixed for retinal dissection and protein extraction, or fixed and enucleated and choroids stained for isolectin-B4 and examined.

During topical administration SRPIN340 or SPHINX7 were made up into a gel based drug delivery vehicle to aid duration of drug exposure to the eye (Doukas et al., 2008), 0.05% DMSO was used to dissolve SRPIN340 and was added to control vehicle.

In Vivo Prostate Tumour Study $1\times10^6$ PC-3 RFP (red fluorescent protein) cells were injected surgically in the prostate gland of nude mice. The tumour volume was measured using an IVIS Lumina imaging system twice every week (expressed as total flux: photonssec). Mice were treated three times a week with IP injections of either 20 µg SPHINX, or vehicle, once tumours reached $2\times10^9$ mean photonssec. After 31 days, mice were culled and tumours extracted for further analysis. N=9, p<0.01, two way ANOVA.

Mass Spectrometry

A mass spectrometry based strategy was employed to determine the pharmacokinetics of SRPIN340 in vivo. Initially SRPIN340 and molecular derivative MVRL09 were serially diluted in water (initial stock dissolved in DMSO) from 100 µg/ml to 0 µg/ml and analysed. The chromatograms produced clear peaks at the expected molecular weights for SRPIN340 (349.1 Da) and MVRL09 (351 Da). The area under the peaks were integrated and plotted against concentration to confirm a linear response was observed. SRPIN340 was investigated in eye tissue following 20 ng intravitreal injection and in eye tissue following a single topical application of 5 µg. After a single administration mice were euthanized at time points 1, 4, 8, 24 and 48 hours. Samples, SRPIN340 (the analyte) and control treated, were homogenized and proteins were precipitated out of the samples with an equal volume (100 µl) acetonitrile or acetone.

An internal standard of 100 ng/ml MVRL09 was added to samples to account for any loss of samples during preparation. The solutions of 50% sample and 50% acetonitrile and 100 ng/ml MVRL09 were centrifuged for 15 minutes at 4° C. to pellet the proteins and the supernatant taken for analysis. Solutions were evaporated at 37° C. for eight hours and resuspended in 30 µl acetonitrile ready for injection and MALDI-TOF mass spectrometry analyser (Absciex). Each sample was run for five minutes and chromatograms produced. Standard curves were produced in both human plasma water matrices to determine concentration. Half life was calculated using Prism by fitting a one phase exponential decay to the sample concentrations from 1 hr to 48 hrs using a log plot.

Statistical Analyses

If not indicated otherwise, data are shown as mean±SEM. All data, graphs and statistical analyses were calculated with Microsoft Excel (Microsoft Office Software), GraphPad Prism (GraphPad Software Inc.) and Image J. All results were considered statistically significant at p<0.05 (*), p<0.01 () and p<0.001 (*).

Results

Identification of Novel SRPK1 Inhibitors

Figure 7:
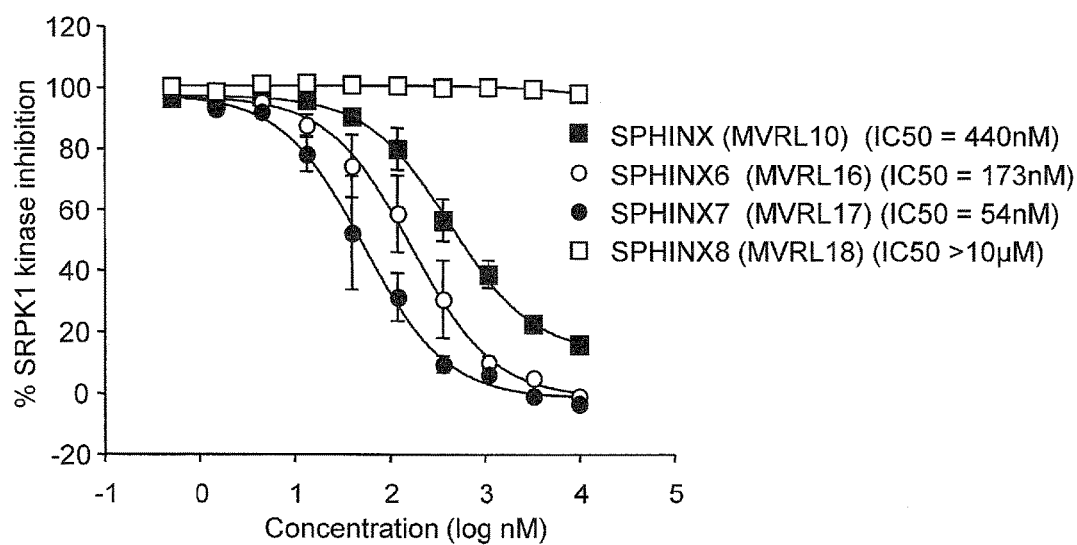
FIG. 7 shows the level of SRPK1 inhibition of the compounds SPHINX, SPHINX6, SPHINX7 and SPHINX8 as defined in Formula (Ia) and Table 1 in an in vitro assay.
Figure 8:
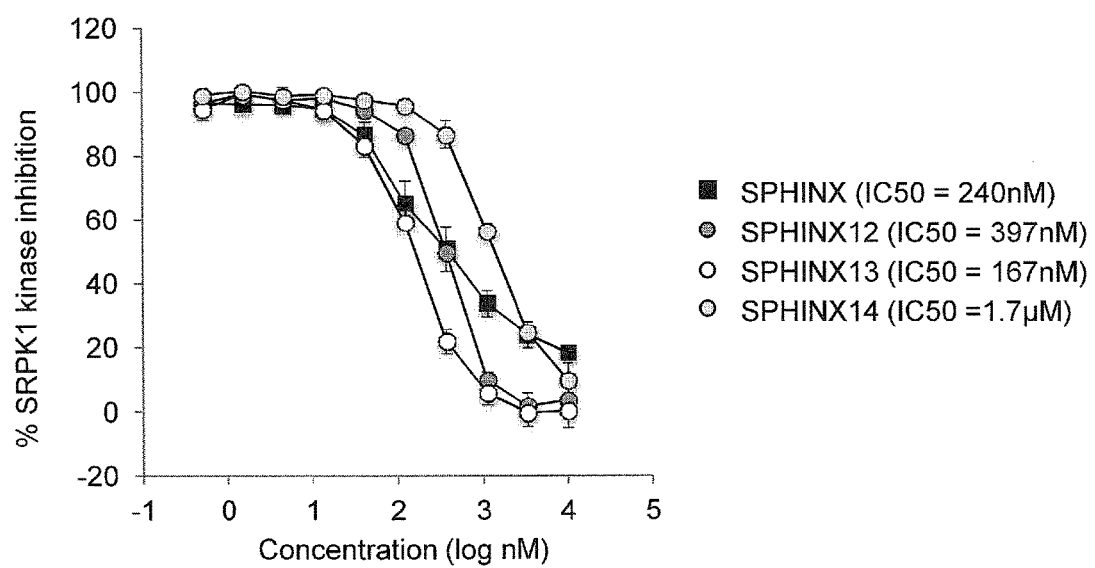
FIG. 8 shows the level of SRPK1 inhibition of the compounds SPHINX, SPHINX12 SPHINX13 and SPHINX14 as defined in Formula (Ia) and Table 1 in an vitro kinase assay.

To identify novel SRPK1 and highly related SRPK2 inhibitors, a range of inhibitors were screened in an in vitro kinase assay (Promega; Koresawa and Okabe, 2004). The previously identified SRPK inhibitor SRPIN340 (Fukuhara et al., 2006) was used as a positive control for the identification of novel candidate compounds MVRL10 (5-methyl-N-[2-(morpholin-4-yl)-5-(trifluoromethyl)phenyl]furan-2-carboxamide) and MVRL09 (N-[2-(morpholin-4-yl)-5-(trifluoromethyl)phenyl]pyridine-3-carboxamide). The structural derivative SRPIN349 was used as a negative control (FIG. 1). SRPIN349 has the same structure as SRPIN340 but with a hydrogen atom in place of the trifluoromethyl moiety. All three inhibitors showed some ability to inhibit the SRPK1 kinase, MVRL09 being the least effective with an $IC_{50}$ greater than 10 µM. Both SRPIN340 and MVRL10 potently inhibited SRPK1 activity with $IC_{50}$ values of 0.96 µM and 0.85 µM, respectively (FIG. 1B). The results gained in this assay are consistent with the published $IC_{50}$ for SRPIN340 (0.8904; Fukuhara et al., 2006). Novel candidate compounds MVRL16 (SPHINX6), MVRL17 (SPHINX7) were also identified using the same in vitro kinase assay, exhibiting SRPK1 inhibition with $IC_{50}$ values of 173 nM and 54 nM respectively (FIG. 7). MVRL18 (SPHINX8), SPHINX9 and SPHINX10, in which the piperazine structure is missing exhibited no activity in the in vitro assay.

Subsequently the ability of these compounds to inhibit SRPK2 activity were investigated. SRPIN340 inhibited SRPK2 activity with an $IC_{50}$ of 7.4 µM. MVRL09 showed no inhibition of SRPK2 and MVRL10 showed only 10% kinase inhibition at 10 µM (FIG. 1C). All three compounds preferentially target SRPK1 over SRPK2, but MVRL10 was the most specific, exhibiting a greater than 10 fold preference for SRPK1. A panel of 58 kinases was screened using microcalorimetry, and at 10 µM a temperature shift of greater than 2° C. was seen only for SRPK1)(9.82°, MSSK1A (7.93° C.) and SRPK2 (3.5° C.). All 55 other kinases had <2° C. shift and 52 of them <1° C. shift.

Figure 2:
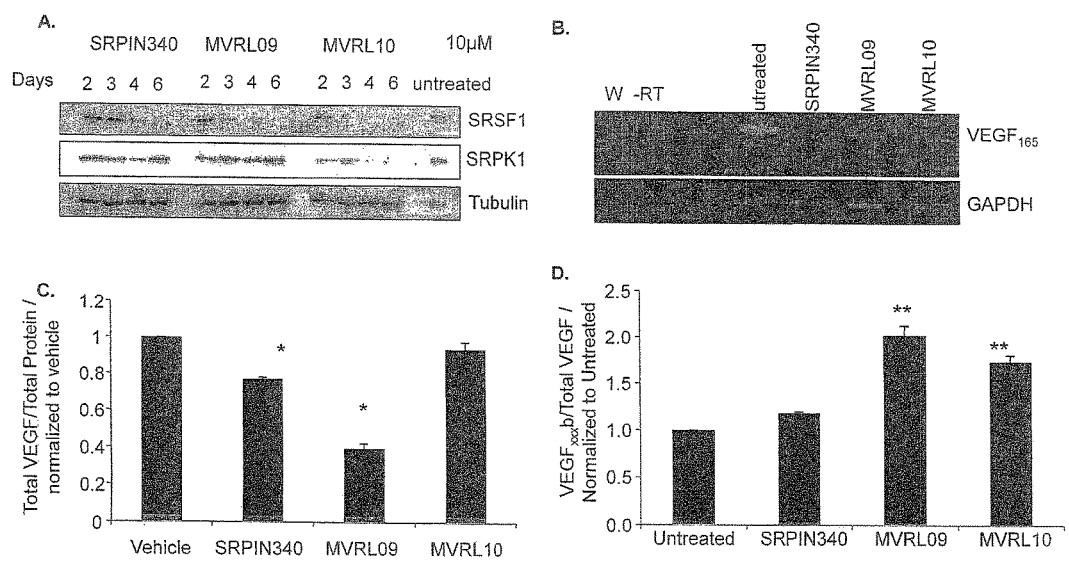
FIG. 2A shows the effects of the compounds of FIG. 1A on SRSF1 expression relative to a tubulin control in ARPE-19 cells.
FIG. 2B shows the effects of the compounds of FIG. 1A on expression of VEGF165 mRNA isoforms relative to GAPDH in primary RPE cells.
FIG. 2C shows the effects of the compounds of FIG. 1A on VEGF expression relative to total protein.
FIG. 2D shows the effects of the compounds of FIG. 1A on the ratio of $VEGFxxx_b$/Total VEGF expression.

The SRPK inhibitors were tested in a series of in vitro assays to determine the effect of treatment on VEGF isoform expression. Initially the effect of compound treatment on SRPK1 and SRSF1 expression was determined. Previous publications had suggested SRSF1 phosphorylation by SRPK1 leads to the nuclear localisation of SRSF1 enabling its binding to VEGF pre mRNA where it can facilitate splicing (Nowak et al., 2008; Nowak et al., 2010; Amin et al., 2011). We observed 10 µM treatment of SRPIN340 and MVRL09 failed to affect SRPK1 expression even after six days of treatment in ARPE-19 cells. MVRL10 did appear to reduce SRPK1 expression suggesting it may alter the stability of the kinase (FIG. 2A). Treatment of ARPE-19 cells with SRPIN340, MVRL09 and MVRL10 reduced expression of SRSF1 relative to a tubulin control after 72 hours treatment times and extending up to six days (FIG. 2A).

Inhibitor treatment for 24 hours at 5 µM altered the expression of $VEGF_{165}$ mRNA isoforms relative to GAPDH in primary RPE cells. All three inhibitors reduced the expression of $VEGF_{165}$ and MVRL09 induced clear expression of $VEGF_{165}b$ (FIG. 2B). We went onto investigate the effect of SRPK1 inhibition on VEGF protein expression. SRPIN340 and MVRL09 significantly reduced VEGF expression relative to total protein but MVRL10 failed to elicit any effect (FIG. 2C). To determine whether MVRL10 altered the ratio of VEGF pro and anti-angiogenic isoforms we performed panVEGF and $VEGF_{xxx}b$ specific ELISAs. All three inhibitors increased the ratio of $VEGF_{xxx}b$/Total VEGF with MVRL09 and MVRL10 being highly significant (p<0.01), suggesting SRPK1 inhibition reduces the expression of pro-angiogenic VEGF, promotes the expression of anti-angiogenic VEGF or a combination of both (FIG. 2D).

MVRL10 therefore appeared to be a relatively specific inhibitor of SRPK1. To determine whether SRPK1 inhibition could inhibit CNV in animal models we tested these compounds alongside each other in a laser-induced mouse CNV model. Two intravitreal injections of 10 ng SRPIN340 and MVRL10 each significantly reduced neovascular area compared to control injected eyes to a similar extent (p<0.05, FIG. 3A). To determine whether SRPIN340 could alter VEGF expression in the retina in which CNV was reduced, a rat model of laser induced CNV was used, as mouse monoclonal antibodies to VEGF isoforms cannot be easily used in mouse tissues, due to the potential detection of mouse IgG (which runs similarly to VEGF). SRPIN340 was tested alongside the VEGF antibody, G6-31 (Roche). SRPIN340 injection (25 ng) again significantly reduced the CNV area compared to saline injected controls (p<0.05). The VEGF antibody G6-31 resulted in a non-significant effect on CNV area in this rat model (FIG. 3B), although it did result in a reduction in a mouse CNV model (Rennel et al, 2011).

Figure 3:
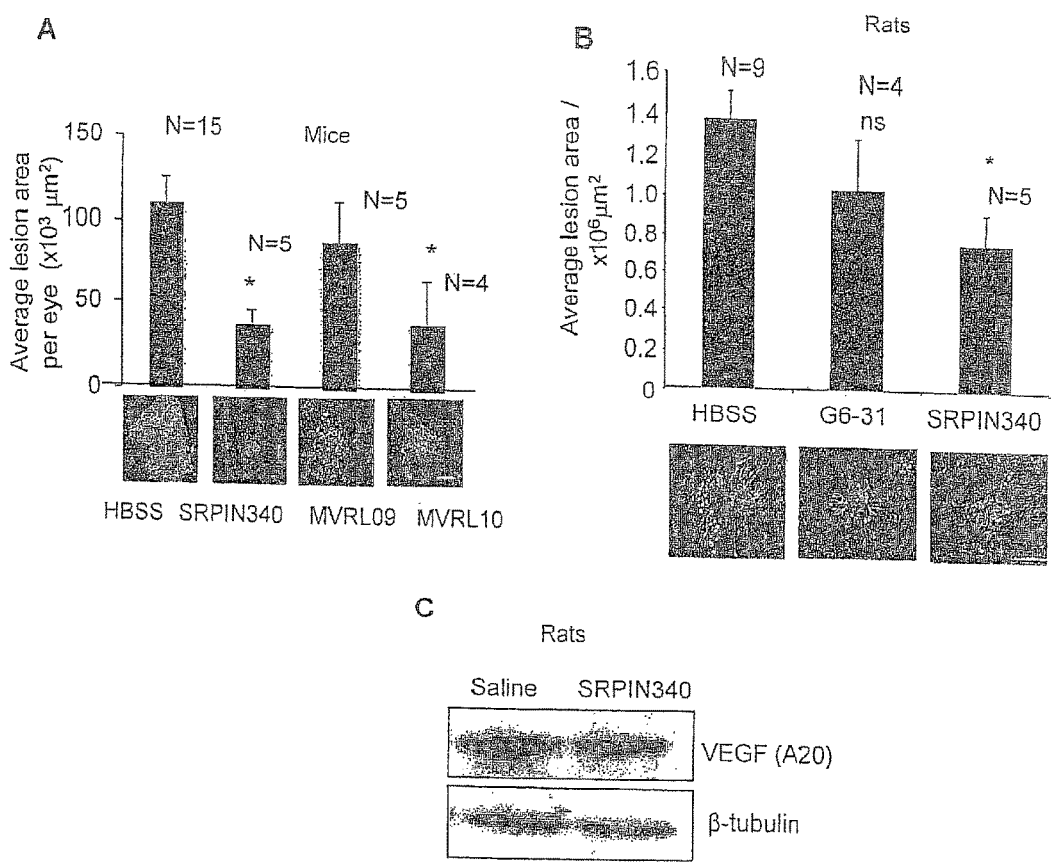
FIG. 3A shows the effects of the compounds of FIG. 1A in a laser-induced mouse CNV model.
FIG. 3B shows the effects of SRPIN340 on VEGF expression in a laser-induced rat CNV model, compared to the VEGF antibody G6-31.
FIG. 3C shows the effects of SRPIN340 on VEGF expression in retinal protein from eyes treated with SRPIN340.
Figure 6:
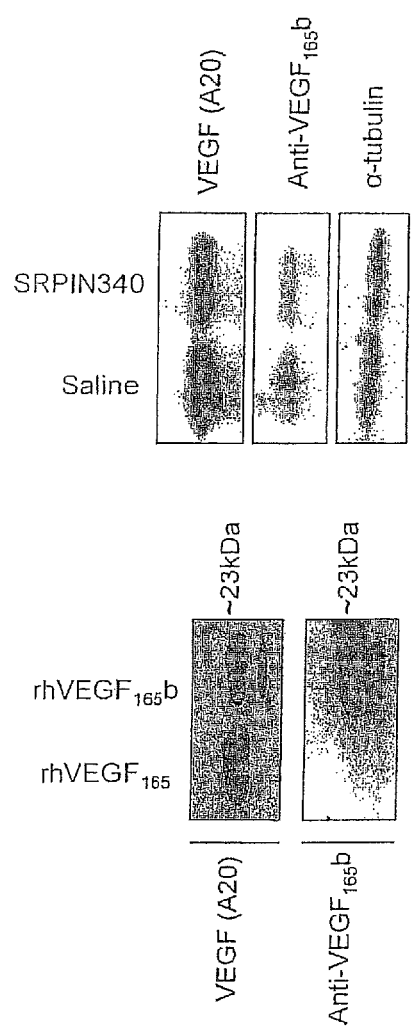
FIG. 6 shows the ratio of pro to anti-VEGF isoforms in retinal protein following SRPIN340 treatment.

Retinal protein from SRPIN340 and saline treated eyes 4 days after initial treatment was assessed for VEGF expression by western blot. A decrease in the expression of VEGF was observed in SRPIN340 treated eyes (FIG. 3C). The expression of $VEGF_{xxx}b$ isoforms was investigated using mouse monoclonal 561 antibody (R&D systems). No difference in the ratio of pro to anti-VEGF isoforms was observed in retinal protein following SRPIN340 treatment at this time point (FIG. 6).

Figure 4:
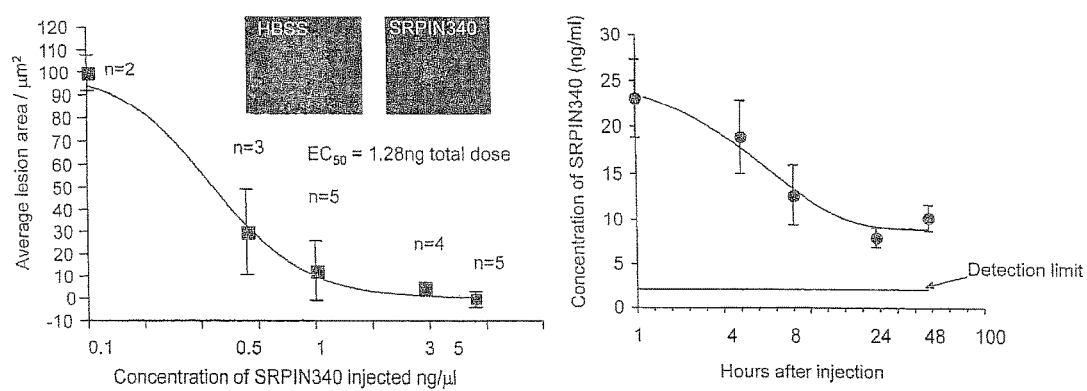
FIG. 4A shows the dose-dependent nature of inhibition of laser-induced CNV by SRPIN340.
FIG. 4B shows the half-life curve of SRPIN340 in the eye following intravitreal injection.

To determine the potency of SRPK1 inhibition by SRPIN340 at inhibiting laser-induced CNV in the mouse a dose-escalation study was performed. SRPIN340 dose-dependently reduced CNV area compared to control injected eyes with an $EC_{50}$ of 1.28 ng total injected dose (FIG. 4A). We went on to determine pharmacokinetics of SRPIN340 in the eye following intravitreal injection. Injection of 20 ng resulted in a relatively long and sustainable concentration of >10 ng/ml in the eye over a 2 day period. Curve fitting to the concentrations measured at 1, 4, 8 24 and 48 hours gave an estimated sustained half-life of 22 hrs (FIG. 4B).

Based on its low molecular weight and favourable drug qualities (MW349, Log P 3.68 and satisfies Lipinski's rule of 5), we hypothesized that SRPIN340 and related compounds may be capable of preventing VEGF mediated CNV when administered topically as an eye drop. We performed a dose response trial investigating SRPIN340 topical eye drops. SRPIN340 was dissolved in a previously described drug delivery vehicle (Doukas et al., 2008) and administered twice daily. Fourteen days following laser insult choroids were fixed and flatmounted for isolectin staining and retinae were extracted for RNA analysis.

Figure 5:
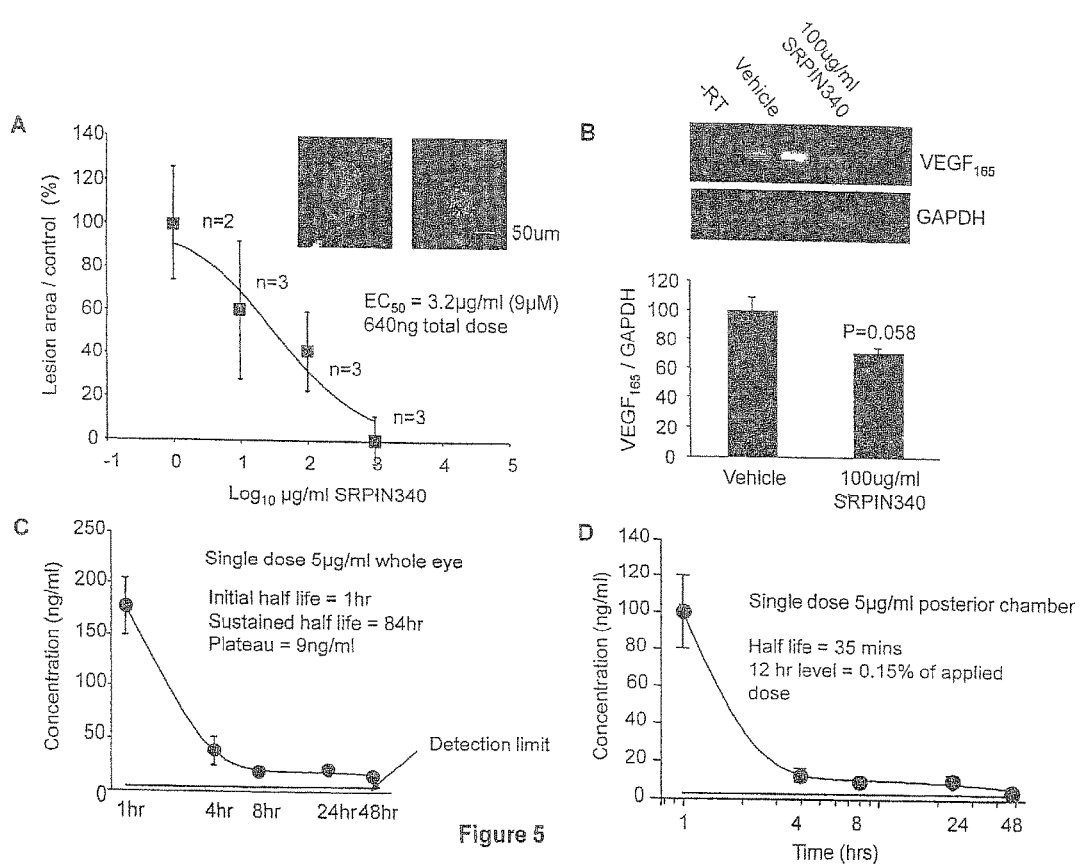
FIG. 5A shows the effect of topically administered SRPIN340 drops on CNV lesion area.
FIG. 5B shows the effect of topically administered SRPIN340 on $VEGF_{165}$ mRNA expression in the retina.
FIG. 5C shows the half-life curve of SRPIN340 in the whole eye following topical administration.
FIG. 5D shows the half-life curve of SRPIN340 in the posterior chamber of the eye following topical administration.

Topical SRPIN340 drops dose dependently reduced CNV lesion area with an $EC_{50}$ of 640 ng total dose, 500 times the concentration required to achieve the same effect following SRPIN340 intravitreal injection (FIG. 5A). Furthermore $VEGF_{165}$ mRNA expression in the retinae was reduced following SRPIN340 treatment (p=0.058) (FIG. 5B). To confirm SRPIN340 was detectable in the eye following topical administration mass spectrometry was performed. A single drop of 5 μg in 10 μl vehicle SRPIN340 was administered to one eye of CD-1 mice and a control vehicle was administered to the other. After 1, 4, 8, 24 and 48 hours mice were culled and eye tissue from the anterior and posterior chamber of the eye was separately analysed for SRPIN340 expression. SRPIN340 was detected both in the whole eye and specifically in the posterior chamber. After 1 hour 3.5% of the total applied dose was detected in the eye (FIG. 5C). In the posterior chamber, composed of retina, sclerochoroidal complex and residual vitreous, 0.15% of the applied dose was detected after 12 hours (FIG. 5D). Exponential decay analysis using prism software generated an initial half-life in the posterior chamber of 35 minutes.

Discussion

Figure 9A:
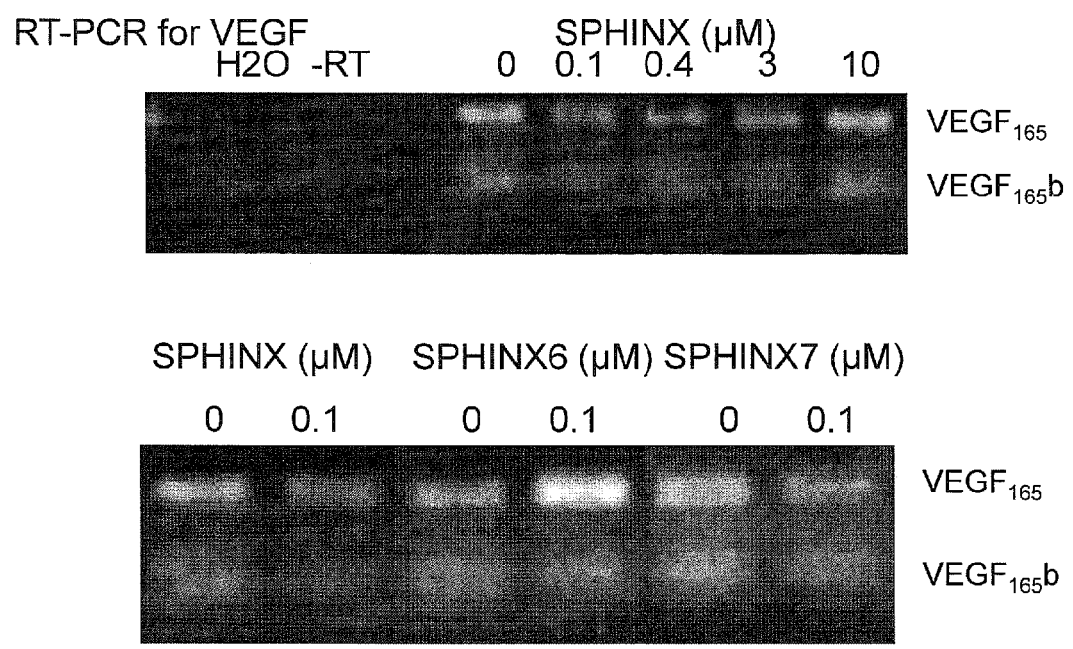
FIG. 9A shows the effect of SPHINX6 and 7 on $VEGF_{165}b$ RNA transcription.
Figure 9B:
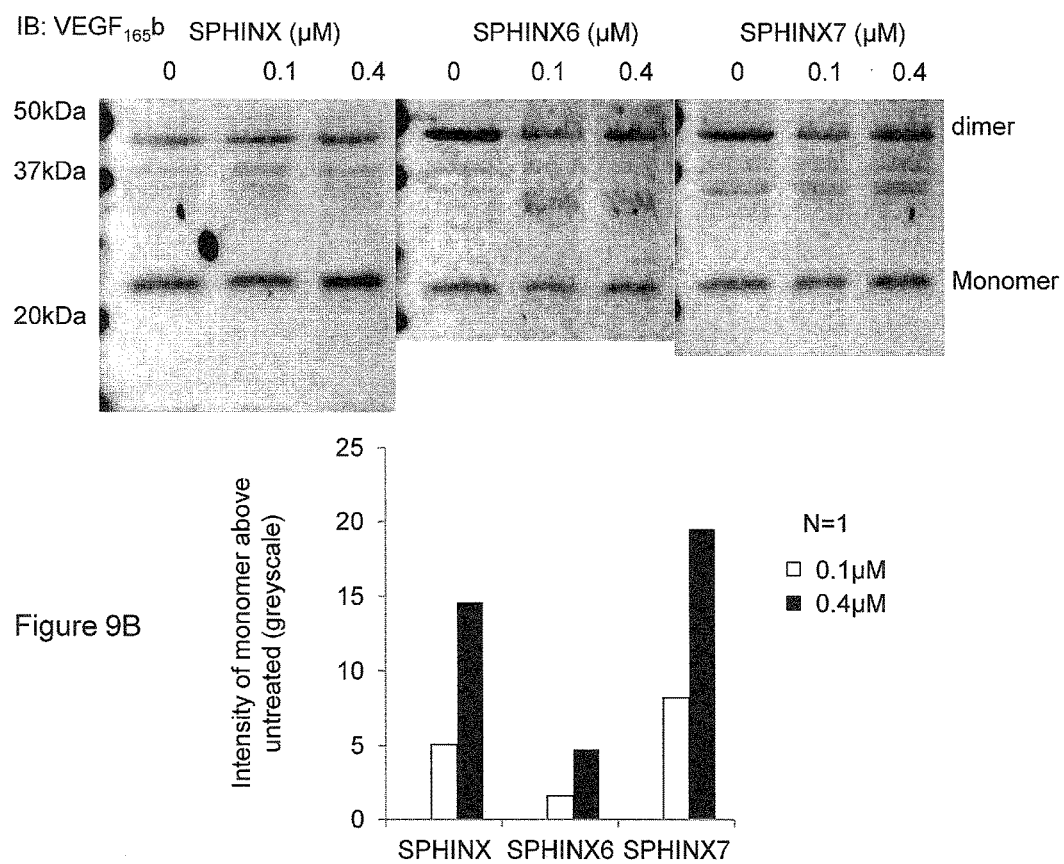
FIG. 9B shows the effect of SPHINX6 and 7 on $VEGF_{165}b$ protein expression.
Figure 10A:
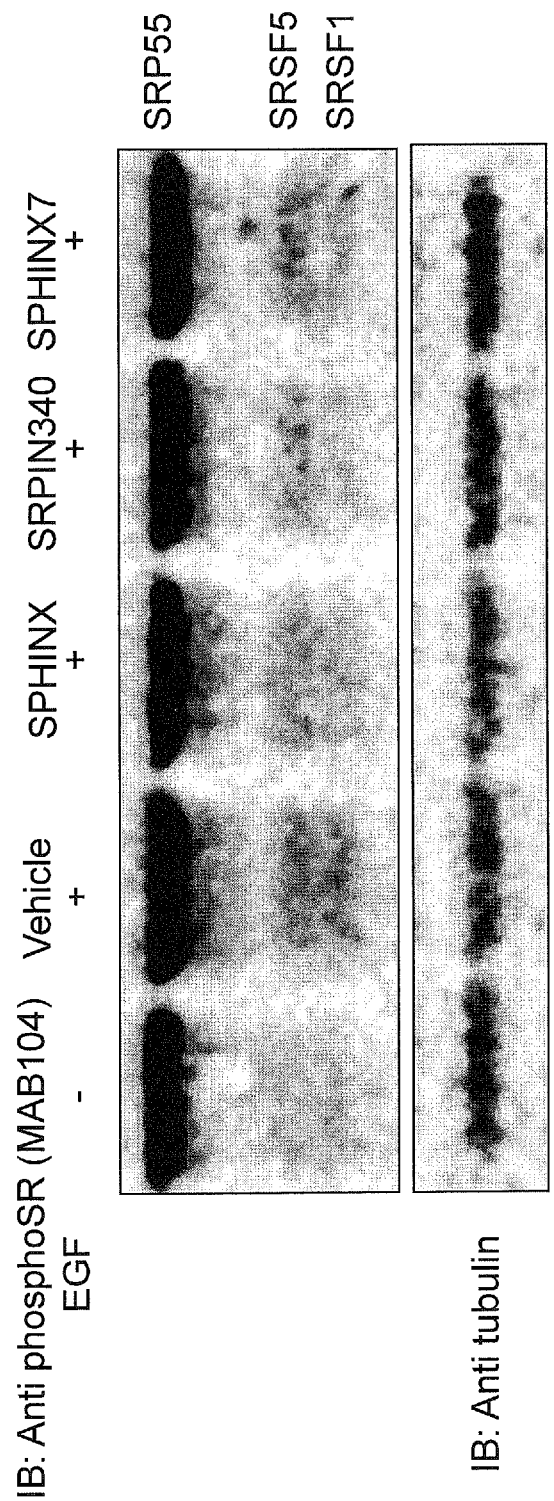
FIGS. 10A and 10B show that SPHINX7 inhibits SRSF1 phosphorylation induced by EGF activation.
Figure 10B:
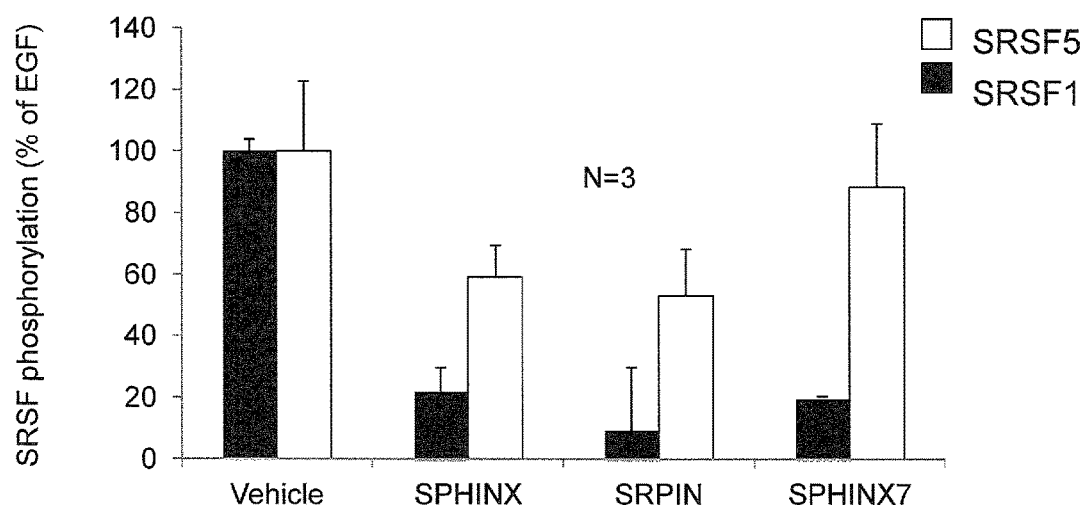
Figure 11:
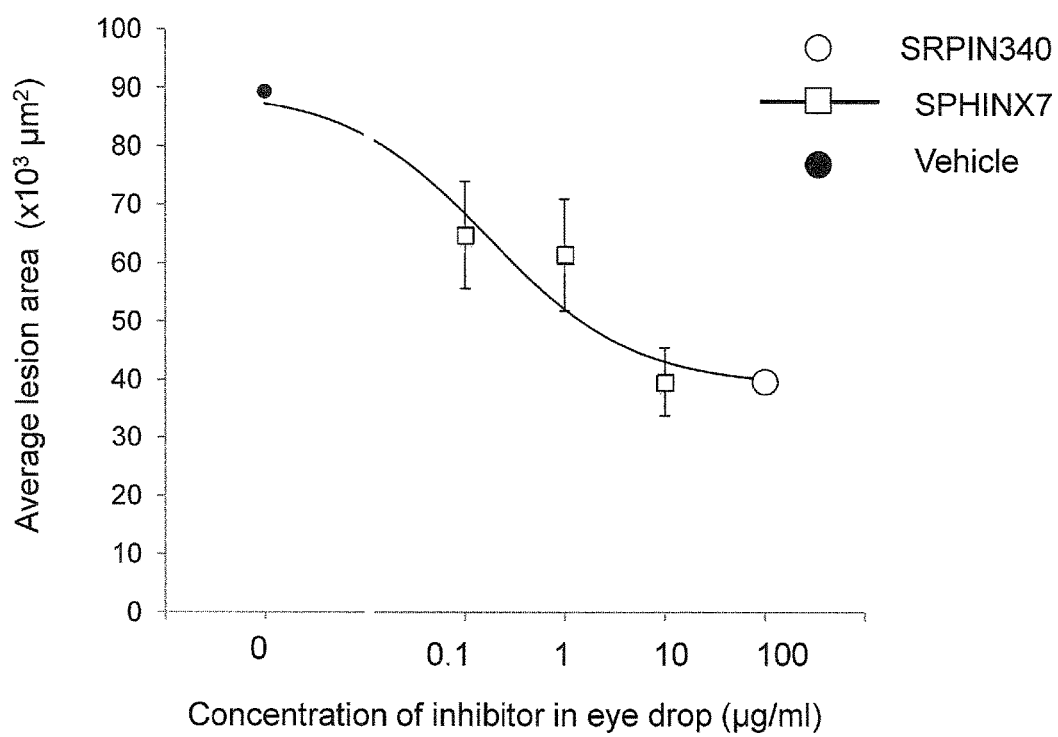
FIG. 11 shows that SPHINX7 inhibits angiogenesis in the eye as an eye drop. SRPIN340 and SPHINX7 significantly inhibited CNV formation. The $IC_{50}$ for SPHINX7 was 225 ng/ml.
Figure 12:
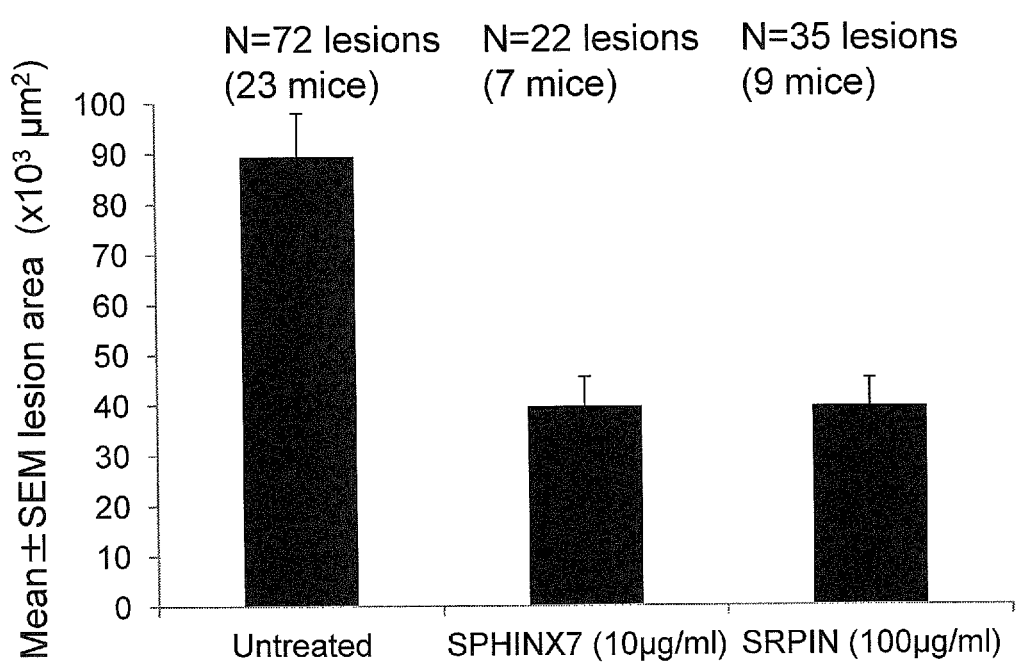
FIG. 12 shows further data that demonstrates that SPHINX7 inhibits angiogenesis in the eye as an eye drop.
Figure 13:
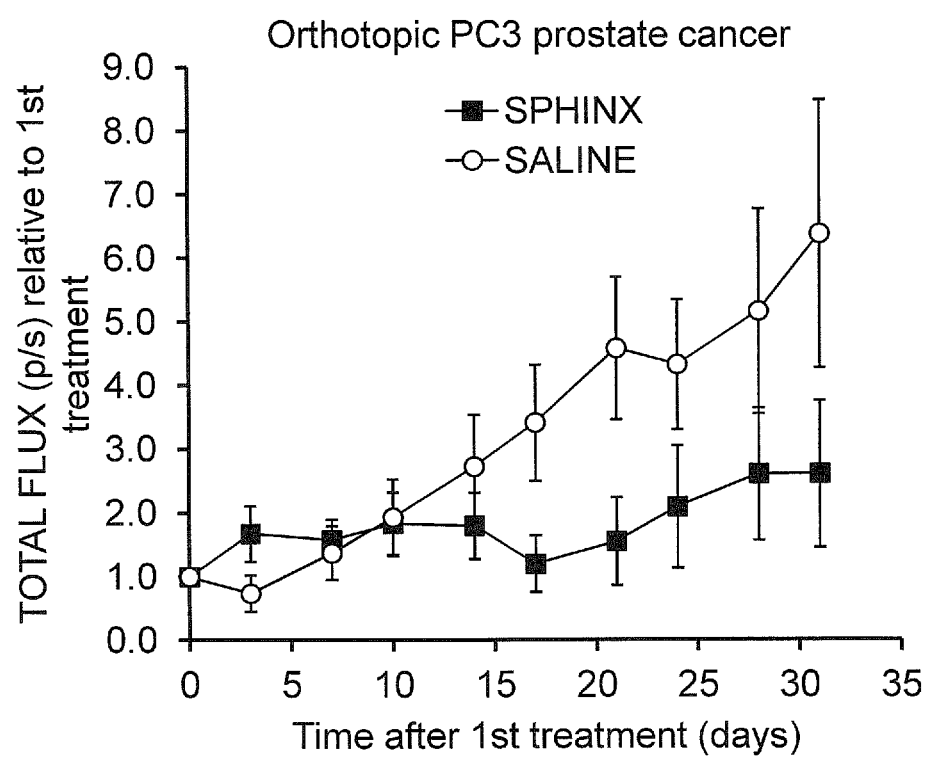
FIG. 13 demonstrates inhibition of prostate tumour growth by targeting SRPK1.

We have used small molecule compound inhibitors of SRPK1 to reduce the expression of pro-angiogenic VEGF isoform $VEGF_{165}$ and inhibit CNV in vivo. We identified inhibitors that prevented SRPK1 phosphorylation of the SRSF1 RS domain serine residues in vitro. The interaction of SRSF1 with SRPK1 is well described in the literature (Aubol et al., 2003; Velazquez-Dones et al., 2005; Ngo et al., 2005). SRSF1 is a protooncogene SR protein that regulates the alternative splicing of numerous genes, including VEGF (Sanford et al., 2005). Here we have shown repeated administration of SRPK1 inhibitors to ARPE-19 cells reduced the expression of SRSF1 independent of SRPK1 expression suggesting phosphorylation of SRSF1 could be necessary for its cytoplasmic stability. Furthermore SRPK1 inhibitors SRPIN340 and MVRL09 reduced the expression $VEGF_{65}$ at RNA level and significantly reduced total VEGF expression at protein level. MVRL10 failed to affect VEGF protein levels, however further investigation into the expression ratio of pro- and anti-angiogenic VEGF isoforms showed MVRL10 significantly switched the ratio to favour the expression of anti-angiogenic VEGF isoforms. SPHINX7 at 100 nM has been shown to reduce the amount of $VEGF_{165}$ at RNA level (FIG. 9A), increase $VEGF_{165}b$ at protein level (FIG. 9B), and inhibit SRSF1 phosphorylation at 10 μM (FIGS. 10A and 10B). When tested in vivo in a mouse laser-induced CNV model all three inhibitors reduced the area of neovascular lesions with SPHINX7, SRPIN340 and MVRL10 (SPHINX) achieving significance.

Although a switch in VEGF splicing to anti-angiogenic VEGF isoforms was observed during SRPK1 inhibition in human primary RPE and ARPE-19 cell lines, detection of $VEGF_{xxx}b$ isoforms remains to be definitively shown in mouse tissues. Both mRNA (detected by qPCR (Xu et al 2011, Zhao et al exp eye res, Caires et al Endocrinology) and protein (identified by Western blot (Zhao et al) have been described in mouse, but for both methods, the lack of stringent controls (excluding IgG contamination or cross amplification) could argue against $VEGF_{65}b$ expression (Harris et al). It has been suggested that the alternative splicing of VEGF transcripts increases during evolution with $VEGF_{165}b$ expression being very low in normal mice increasing through rabbits and pigs to highest expression in primates (Xu et al 2011). Thus in the mouse model SRPK1 inhibitors may prevent CNV by reducing the expression of pro-angiogenic VEGF isoforms either by preventing the use of the proximal splice site, resulting in reduction of mature RNA, or through indirect alterations in transcriptional or translational regulation. Currently no investigations have identified the regulators of VEGF alternative splicing in mice. When tested in a laser-induced rat CNV model SRPIN340 (Fukuhara et al., 2006) reduced CNV area and total VEGF protein expression. $VEGF_{xxx}b$ expression was investigated in the rat retinae, $VEGF_{xxx}b$ was expressed but no change in the expression of $VEGF_{xxx}b$ isoforms was observed during SRPIN340 treatment compared to saline controls at that time point, suggesting in rodent models SRPK1 inhibition may be anti-angiogenic by reducing pro-angiogenic VEGF expression.

We went onto determine the $EC_{50}$ of SRPIN340 on CNV area in the mouse model. SRPIN340 produced at $EC_{50}$ of 1.28 ng and the dose range of SRPIN340 used, 0.2-10 ng/eye, was similar to the dose of $rhVEGF_{165}b$ previously used to inhibit CNV (Hua et al., 2010). Hua and colleagues determined an effective $rhVEGF_{165}b$ dose in humans of 3

µg/eye, 1000- to 10-fold lower than ranibizumab or bevacizumab (Brown et al., 2006). It is difficult to directly compare human specific Ranibizumab to the SRPIN340 efficacy data in mouse, compared to rhVEGF-$A_{165}$b SRPIN340 was 160 times less effective (Hua et al., 2010) but required a dose 125 times less than pegaptanib in rodents (Ishida et al., 2003). The data suggests SRPIN340 has the potential to achieve similar reductions in CNV as current treatment Ranibizumab at lower doses following intravitreal injection.

One of the drawbacks of Ranibizumab treatment is the need for monthly intraocular injections, thus we investigated whether SRPIN340 and SPHINX7 could potently inhibit CNV following topical administration. Topical SRPIN340 significantly suppressed CNV in mice with an $EC_{50}$ of 3.187 µg/ml, 500 times greater than injected SRPIN340. Pharmacokinetic analysis suggested 3.5% of the topically applied dose was detected in the eye after 1 hour reflecting previous estimations that due to poor ocular bioavailability only 5% of a topically applied drug will get into the eye (Geroski and Edelhauser, 2000). Furthermore, SRPIN340 was still detectable in the eye 48 hours after a single topical administration but was not detected systemically. Despite only approximately 5% of applied SRPIN340 being likely of penetrating the eye the dose required to achieve 50% CNV inhibition using topical SRPIN340 compares favourably to other topical therapies.

In 2008 Doukas and colleagues identified TG100801, an inactive pro-drug that generates TG100572 by de-esterification. TG100801 targets Src kinases and selected tyrosine receptor kinases including VEGFR-1 and VEGFR-2, twice daily topical application of 1% but not 0.6% TG100801 significantly reduced CNV lesion area (Doukas et al., 2008), however 0.01% SRPIN340 solution in the same drug delivery vehicle produced a significant inhibition of CNV area. To our knowledge SRPIN340 and SPHINX7 are the first topical compounds to alter the expression of pro-angiogenic VEGF isoforms. Following topical SRPIN340 treatment mouse retinae assessed for $VEGF_{165}$ expression showed a near significant reduction in $VEGF_{165}$ (p=0.058; n=3). $VEGF_{165}$, the more potently mitogenic VEGF isoform (Keyt et al., 1996) is sufficient for physiological neovascularization during retinal development (Stalmans et al., 2002). This study has focused on investigating $VEGF_{165}$ expression following SRPK1 inhibition; however, we predict the expression of other pro-angiogenic VEGF isoforms such as $VEGF_{121}$ will also be reduced following SRPK1 inhibition. Indeed it has been shown that SRSF1 binds to human VEGF pre-mRNA in a region 35nt prior to the VEGF exon eight PSS, a splice site conserved both across species and by all pro-angiogenic VEGF isoforms (Amin et al., 2011).

Treatment of induced prostate cancer in nude mice with IP injections of 20 µg SPHINX three times a week for 30 days led to a significant reduction in the tumour volume relative to a control saline injection (measured as total flux: photonssec), demonstrating that the claimed compounds are also effective at inhibiting angiogenesis so can be used in anti-angiogenic treatment of mammalian subjects, for example treatment of cancer in mammalian subjects.

The data presented in this study suggests SRPK1 as a novel target for small molecular weight compound inhibitors in reducing pro-angiogenic VEGF mediated CNV associated with AMD. Furthermore we have shown that the compounds of the present invention are effective at reducing CNV following topical administration in mice, and for reducing tumour growth in mice when injected.

TABLE 1

$IC_{50}$ data for compounds of Formula (Ia) tested in the SRPK1 inhibition assay

| Name | W | $R_8$ | IC50 (nM) for SRPK1 |
|---|---|---|---|
| SPHINX (MVRL10) | N-morpholinyl | $CH_3$ | 440 |
| SPHINX6 (MVRL16) | N-methylpiperazinyl-ethyl-N-methylamino | 3-pyridyl | 177 |
| SPHINX7 (MVRL17) | N-methylpiperazinyl-ethyl-N-methylamino | 4-pyridyl | 54.7 |
| SPHINX8 (MVRL18) | NH-ethyl-N-methylamino | 3-pyridyl | 9307 |
| SPHINX9 | NH-CH2-(3-pyridyl) | 3-pyridyl | >10000 |
| SPHINX10 | NH-CH2-(3-pyridyl) | 4-pyridyl | >10000 |
| SPHINX12 | N-methylpiperazinyl | 3-pyridyl | 367 |

TABLE 1-continued

IC$_{50}$ data for compounds of Formula (Ia) tested in the SRPK1 inhibition assay

| Name | W | R$_8$ | IC50 (nM) for SRPK1 |
|------|---|-------|---------------------|
| SPHINX13 | 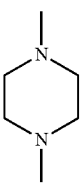 | 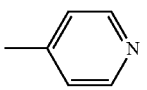 | 162 |
| SPHINX14 | 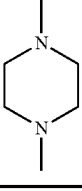 | CN | 1268 |

REFERENCES

Bressler, S., Bressler, N. M., Clemons, T., Ferris, F. L., Milton, R. C., Klien, R., Klien, B. and Age-Related Eye Dis Study, G. (2004) 'Ocular risk factors for developing neovascular AMD in the fellow eyes of patients with unilateral neovascular AMD', *Investigative Ophthalmology & Visual Science*, 45, U924-U924.

Ferris, F. L., Fine, S. L. and Hyman, L. (1984) 'Age-related macular degeneration and blindness due to neovascular maculopathy', *Archives of Ophthalmology*, 102(11), 1640-1642.

Patz, A., Fine, S. L., Finkelstein, D. and Yassur, Y. (1977) 'Diseases of macula—diagnosis and management of choroidal neovascularization', *Transactions American Academy of Ophthalmology and Otolaryngology*, 83(3), 468-475.

Fine, S. L., Berger, J. W., Maguire, M. G. and Ho, A. C. (2000) 'Drug therapy: Age-related macular degeneration', *New England Journal of Medicine*, 342(7), 483-492.

Campochiaro, P. A., Nguyen, Q. D., Shah, S. M., Klein, M. L., Holz, E., Frank, R. N., Saperstein, D. A., Gupta, A., Stout, J. T., Macko, J., DiBartolomeo, R. and Wei, L. L. (2006) 'Adenoviral vector-delivered pigment epithelium-derived factor for neovascular age-related macular degeneration: Results of a phase I clinical trial', *Human Gene Therapy*, 17(2), 167-176.

Dvorak, H. F., Brown, L. F., Detmar, M. and Dvorak, A. M. (1995) 'Vascular-permeability factor vascular endothelial growth-factor, microvascular hyperpermeability, and angiogenesis', *American Journal of Pathology*, 146(5), 1029-1039.

D'Amore, P. A., Shima, D. T., Adamis, A. P., Yeo, K. T., Yeo, T. K., Allende, R. and Folkman, J. (1994) 'differential regulation of VEGF/VPF and basic FGF by hypoxia', *Faseb Journal*, 8(4), A116-A116.

Spilsbury, K., Garrett, K. L., Shen, W. Y., Constable, I. J. and Rakoczy, P. E. (2000) 'Overexpression of vascular endothelial growth factor (VEGF) in the retinal pigment epithelium leads to the development of choroidal neovascularization', *American Journal of Pathology*, 157(1), 135-144.

Anderson, D. H., Mullins, R. F., Hageman, G. S. and Johnson, L. V. (2002) 'Perspective—A role for local inflammation in the formation of drusen in the aging eye', *American Journal of Ophthalmology*, 134(3), 411-431.

Das, A., Fanslow, W., Cerretti, D., Warren, E., Talarico, N. and McGuire, P. (2003) 'AngiopoietinTek interactions regulate MMP-9 expression and retinal neovascularization', *Laboratory Investigation*, 83(11), 1637-1645.

Leung, D. W., Cachianes, G., Kuang, W. J., Goeddel, D. V. and Ferrara, N. (1989) 'Vascular endothelial growth-factor is a secreted angiogenic mitogen', *Science*, 246 (4935), 1306-1309.

Jingjing, L., Xue, Y., Agarwal, N. and Roque, R. S. (1999) 'Human Muller cells express VEGF183, a novel spliced variant of vascular endothelial growth factor', *Iovs*, 40(3), 752-759.

Houck, K. A., Ferrara, N., Winer, J., Cachianes, G., Li, B. and Leung, D. W. (1991) 'The vascular endothelial growth-factor family—identification of a 4th molecular-species and characterization of alternative splicing of ma', *Molecular Endocrinology*, 5(12), 1806-1814.

Nineur, P., Colige, A. C., Deroanne, C. F., Dubail, J., Kesteloot, F., Habraken, Y., Noel, A., Voo, S., Waltenberger, J., Lapiere, C. M., Nusgens, B. V. and Lambert, C. A. (2007) 'Newly identified biologically active and proteolysis-resistant VEGF-A isoform VEGF111 is induced by genotoxic agents', *Journal of Cell Biology*, 179(6), 1261-1273.

Tischer, E., Gospodarowicz, D., Mitchell, R., Silva, M., Schilling, J., Lau, K., Crisp, T., Fiddes, J. C. and Abraham, J. A. (1989) 'Vascular endothelial growth-factor—a new member of the platelet-derived growth-factor gene family', *Biochemical and Biophysical Research Communications*, 165(3), 1198-1206.

Neufeld, G., Cohen, T., Gengrinovitch, S. and Poltorak, Z. (1999) 'Vascular endothelial growth factor (VEGF) and its receptors', *Faseb Journal*, 13(1), 9-22.

Bates, D. O., Cui, T. G., Doughty, J. M., Winkler, M., Sugiono, M., Shields, J. D., Peat, D., Gillatt, D. and Harper, S. J. (2002) 'VEGF(165)b, an inhibitory splice variant of vascular endothelial growth factor, is downregulated in renal cell carcinoma', *Cancer Research*, 62(14), 4123-4131.

Woolard, J., Wang, W. Y., Bevan, H. S., Qiu, Y., Morbidelli, L., Pritchard-Jones, R. O., Cui, T. G., Sugiono, M., Waine, E., Perrin, R., Foster, R., Digby-Bell, J., Shields, J. D., Whittles, C, E., Mushens, R. E., Gillatt, D. A., Ziche, M., Harper, S. J. and Bates, D. O. (2004) 'VEGF(165)b, an inhibitory vascular endothelial growth factor splice variant: Mechanism of action, in vivo effect on angiogenesis and endogenous protein expression', *Cancer Research*, 64(21), 7822-7835.

Perrin, R. M., Konopatskaya, O., Qiu, Y., Harper, S., Bates, D. O. and Churchill, A. J. (2005) 'Diabetic retinopathy is associated with a switch in splicing from anti- to pro-angiogenic isoforms of vascular endothelial growth factor', *Diabetologia*, 48(11), 2422-2427.

Varey, A. H. R., Rennel, E. S., Qiu, Y., Bevan, H. S., Perrin, R. M., Raffy, S., Dixon, A. R., Paraskeva, C., Zaccheo, O., Hassan, A. B., Harper, S. J. and Bates, D. O. (2008) 'VEGF(165)b, an antiangiogenic VEGF-A isoform, binds and inhibits bevacizumab treatment in experimental colorectal carcinoma: balance of pro- and antiangiogenic VEGF-A isoforms has implications for therapy', *British Journal of Cancer*, 98(8), 1366-1379.

Pritchard-Jones, R. O., Dunn, D. B. A., Qiu, Y., Varey, A. H. R., Orlando, A., Rigby, H., Harper, S. J. and Bates, D. O.

(2007) 'Expression of VEGF(xxx)b, the inhibitory isoforms of VEGF, in malignant melanoma', *British Journal of Cancer,* 97(2), 223-230.

Hua, J., Spee, C., Kase, S., Rennet, E. S., Magnussen, A. L., Qiu, Y., Varey, A., Dhayade, S., Churchill, A. J., Harper, S. J., Bates, D. O. and Hinton, D. R. (2010) 'Recombinant Human VEGF(165)b Inhibits Experimental Choroidal Neovascularization', *Investigative Ophthalmology & Visual Science,* 51(8), 4282-4288.

Magnussen, A. L., Rennel, E. S., Hua, J., Bevan, H. S., Long, N. B., Lehrling, C., Gammons, M., Floege, J., Harper, S. J., Agostini, H. T., Bates, D. O. and Churchill, A. J. (2010) 'VEGF-A(165)b Is Cytoprotective and Antiangiogenic in the Retina', *Investigative Ophthalmology & Visual Science,* 51(8), 4273-4281.

Gragoudas, E. S. (2004) 'VEGF inhibition study in ocular neovascularization-1 (VISION-1): Efficacy results from phase II/III Macugen (TM) (Pegaptanib sodium) clinical trials', *Iovs,* 45(Suppl. 1), U924.

Rosenfeld, P. J., Rich, R. M. and Lalwani, G. A. (2006) 'Ranibizumab: Phase III clinical trial results', *Ophthalmology clinics of North America,* 19(3), 361-72.

Brown, D. M., Kaiser, P. K., Michels, M., Soubrane, G., Heier, J. S., Kim, R. Y., Sy, J. P., Schneider, S. and Grp, A. S. (2006) 'Ranibizumab versus verteporfin for neovascular age-related macular degeneration', *New England Journal of Medicine,* 355(14), 1432-1444.

Brown, D. M., Michels, M., Kaiser, P. K., Heier, J. S., Sy, J. P. and Ianchulev, T. (2009) 'Ranibizumab versus Verteporfin Photodynamic Therapy for Neovascular Age-Related Macular Degeneration: Two-Year Results of the ANCHOR Study', *Ophthalmology,* 116(1), 57-65.

Schmidt-Erfurth, U., Eldem, B., Guymer, R., Korobelnik, J.-F., Schlingemann, R. O., Axer-Siegel, R., Wiedemann, P., Simader, C., Gekkieva, M., Weichselberger, A. and Grp, E. S. (2011) 'Efficacy and Safety of Monthly versus Quarterly Ranibizumab Treatment in Neovascular Age-related Macular Degeneration: The EXCITE Study', *Ophthalmology,* 118(5).

Good, T. J. and Kahook, M. Y. (2010) 'The role of endothelin in the pathophysiology of glaucoma', *Expert Opinion on Therapeutic Targets,* 14(6), 647-654.

Jager, R. D., Aiello, L. P., Patel, S. C. and Cunningham, E. T. (2004) 'Risks of intravitreous injection: A comprehensive review', *Retina—the Journal of Retinal and Vitreous Diseases,* 24(5), 676-698.

Nowak, D. G., Amin, E. M., Rennel, E. S., Hoareau-Aveilla, C., Gammons, M., Damodoran, G., Hagiwara, M., Harper, S. J., Woolard, J., Ladomery, M. R. and Bates, D. O. (2010) 'Regulation of Vascular Endothelial Growth Factor (VEGF) Splicing from Pro-angiogenic to Anti-angiogenic Isoforms a novel therapeutic strategy for angiogenesis', *Journal of Biological Chemistry,* 285(8), 5532-5540.

Amin, E. M., Oltean, S., Hua, J., Gammons, M. V. R., Hamdollah-Zadeh, M., Welsh, G. I., Cheung, M.-K., Ni, L., Kase, S., Renne, E. S., Symonds, K. E., Nowak, D. G., Royer-Pokora, B., Saleem, M. A., Hagiwara, M., Schumacher, V. A., Harper, S. J., Hinton, D. R., Bates, D. O. and Ladomery, M. R. (2011) 'WT1 Mutants Reveal SRPK1 to Be a Downstream Angiogenesis Target by Altering VEGF Splicing', *Cancer Cell,* 20(6), 768-780.

Sanford, J. R., Ellis, J. D., Cazalla, D. and Caceres, J. F. (2005a) 'Reversible phosphorylation differentially affects nuclear and cytoplasmic functons of splicing factor 2/alternative splicing factor', *Proceedings of the National Academy of Sciences of the United States of America,* 102(42), 15042-15047.

Nowak, D. G., Woolard, J., Amin, E. M., Konopatskaya, O., Saleem, M. A., Churchill, A. J., Ladomery, M. R., Harper, S. J. and Bates, D. O. (2008) 'Expression of pro- and anti-angiogenic isoforms of VEGF is differentially regulated by splicing and growth factors', *Journal of Cell Science,* 121(20), 3487-3495.

Doukas, J., Mahesh, S., Umeda, N., Kachi, S., Akiyama, H., Yokoi, K., Cao, J., Chen, Z., Dellamary, L., Tam, B., Racanelli-Layton, A., Hood, J., Martin, M., Noronha, G., Soli, R. and Campochiaro, P. A. (2008) 'Topical administration of a multi-targeted kinase inhibitor suppresses choroidal neovascularization and retinal edema', *Journal of Cellular Physiology,* 216(1), 29-37.

Fukuhara, T., Hosoya, T., Shimizu, S., Sumi, K., Oshiro, T., Yoshinaka, Y., Suzuki, M., Yamamoto, N., Herzenberg, L. A. and Hagiwara, M. (2006) 'Utilization of host SR protein kinases and RNA-splicing machinery during viral replication', *Proceedings of the National Academy of Sciences of the United States of America,* 103(30), 11329-11333.

Rennel, E. S., Regula, J. T., Harper, S. J., Thomas, M., Klein, C. and Bates, D. O. (2011) 'A Human Neutralizing Antibody Specific to Ang-2 Inhibits Ocular Angiogenesis', *Microcirculation,* 18(7).

Aubol, B. E., Chakrabarti, S., Ngo, J., Shaffer, J., Nolen, B., Fu, X. D., Ghosh, G. and Adams, J. A. (2003) 'Processive phosphorylation of alternative splicing factors/plicing factor 2', *Proceedings of the National Academy of Sciences of the United States of America,* 100(22), 12601-12606.

Velazquez-Dones, A., Hagopian, J. C., Ma, C. T., Zhong, X. Y., Zhou, H. L., Ghosh, G., Fu, Y. D. and Adams, J. A. (2005) 'Mass spectrometric and kinetic analysis of ASF/SF2 phosphorylation by SRPK1 and Clk/Sty', *Journal of Biological Chemistry,* 280(50), 41761-41768.

Ngo, J. C. K., Chakrabarti, S., Ding, J. H., Velazquez-Dones, A., Nolen, B., Aubol, B. E., Adams, J. A., Fu, X. D. and Ghosh, G. (2005) 'Interplay between SRPK and Clk/Sty kinases in phosphorylation of the splicing factor ASF/SF2 is regulated by a docking motif in ASF/SF2', *Molecular Cell,* 20(1), 77-89.

Xu, J., Dou, T., Liu, C., Fu, M., Huang, Y., Gu, S., Zhou, Y. and Xie, Y. (2011) 'The evolution of alternative splicing exons in vascular endothelial growth factor A', *Gene,* 487(2).

Caires, K. C., de Avila, J. M., Cupp, A. S. and McLean, D. J. (2012) 'VEGFA Family Isoforms Regulate Spermatogonial Stem Cell Homeostasis in Vivo', *Endocrinology,* 153(2).

Zhao, M., Shi, X., Liang, J., Miao, Y., Xie, W., Zhang, Y. and Li, X. (2011) 'Expression of pro- and anti-angiogenic isoforms of VEGF in the mouse model of oxygen-induced retinopathy', *Experimental Eye Research,* 93(6), 921-926.

Harris, S., Craze, M., Newton, J., Fisher, M., Shima, D. T., Tozer, G. M. and Kanthou, C. (2012) 'Do Anti-Angiogenic VEGF (VEGF$_{xxx}$b) Isoforms Exist? A Cautionary Tale', *Plos One,* 7(5).

McFee, R. M., Rozell, T. G. and Cupp, A. S. (2012) 'The balance of proangiogenic and antiangiogenic VEGFA isoforms regulate follicle development', *Cell and Tissue Research,* 349(3).

Ishida, S., Usui, T., Yamashiro, K., Kaji, Y., Amano, S., Ogura, Y., Hida, T., Oguchi, Y., Ambati, J., Miller, J. W., Gragoudas, E. S., Ng, Y. S., D'Amore, P. A., Shima, D. T.

and Adamis, A. P. (2003) 'VEGF$_{164}$-mediated inflammation is required for pathological, but not physiological, ischemia-induced retinal neovascularization', *Journal of Experimental Medicine,* 198(3), 483-489.

Geroski, D. H. and Edelhauser, H. F. (2000) 'Drug delivery for posterior segment eye disease', *Investigative Ophthalmology & Visual Science,* 41(5), 961-964.

Keyt, B. A., Nguyen, H. V., Berleau, L. T., Duarte, C. M., Park, J., Chen, H. and Ferrara, N. (1996) 'Identification of vascular endothelial growth factor determinants for binding KDR and FLT-1 receptors—Generation of receptor-selective VEGF variants by site-directed mutagenesis', *Journal of Biological Chemistry,* 271(10), 5638-5646.

Stalmans, I., Ng, Y. S., Rohan, R., Fruttiger, M., Bouche, A., Yuce, A., Fujisawa, H., Hermans, B., Shani, M., Jansen, S., Hicklin, D., Anderson, D. J., Gardiner, T., Hammes, H. P., Moons, L., Dewerchin, M., Collen, D., Carmeliet, P. and D'Amore, P. A. (2002) 'Arteriolar and venular patterning in retinas of mice selectively expressing VEGF isoforms', *Journal of Clinical Investigation,* 109(3).

Gammons, M. V., Dick, A. D., Harper, S. J., Bates, D. O. (2013) SRPK1 Inhibition Modulates VEGF Splicing to Reduce Pathological Neovascularization in a Rat Model of Retinopathy of Prematurity *Invest. Ophthalmol. Vis. Sci.* vol. 54(8) 5797-5806.

Gammons, M. V., Fedorov, O., Ivison, D., Du, C., Clark, T., Hopkins, C., Hagiwara, M., Dick, A. D., Cox, R., Harper, S. J., Hancox, J. C. and Bates, D. O. (2013) Topical Antiangiogenic SRPK1 Inhibitors Reduce Choroidal Neovascularization in Rodent Models of Exudative AMD *Invest. Ophthalmol. Vis. Sci.* 54(9) 6052-6062.

The invention claimed is:

1. A method of topically treating ocular neovascularisation, comprising topically administering a compound of Formula (I) to a subject in need thereof:

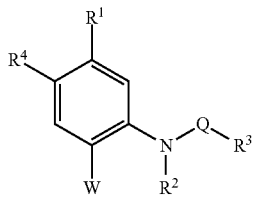

(I)

or a pharmaceutically acceptable salt, solvate, or hydrate; wherein:

$R^1$ represents a $C_{1-6}$ alkyl group which may have one or more substituent, a halogen atom, a nitro group, a cyano group, an azido group, a hydroxy group, a $C_{1-6}$ alkoxy group which may have one or more substituent, a $C_{1-6}$ alkylthio group which may have one or more substituent, a $C_{1-6}$ alkylsulfonyl group which may have one or more substituent, a carboxyl group, a formyl group, a $C_{1-6}$ alkoxycarbonyl group which may have one or more substituent, an acyl group, an acylamino group, or a sulfamoyl group;

$R^2$ represents a hydrogen atom, or a $C_{1-6}$ alkyl group which may have one or more substituent;

$R^3$ represents a nitrogen-containing heterocycle which may have one or more substituent, an oxygen-containing heterocycle which may have one or more substituent, or a condensed aromatic heterocycle which may have one or more substituent;

$R^4$ represents a hydrogen atom or a halogen atom;

Q represents —C(O)—, —C(S)—, —C(S)NHC(O)—, —C(O)NHC(O)—, or C(O)NHC(S)—; and

W represents a 1-piperazinyl group which may have one or more substituents.

2. The method of claim 1, wherein the topical treatment of ocular neovascularisation is dose-dependent treatment or prevention.

3. The method of claim 1, wherein the ocular neovascularisation is choroidal neovascularisation.

4. The method of claim 1, wherein the ocular neovascularisation is retinal neovascularisation.

5. The method according to claim 1, wherein $R^1$ represents a trifluoromethyl group.

6. The method according to claim 1, wherein Q represents —C(O)—.

7. The method according to claim 1, wherein $R^3$ represents an oxygen-containing heterocycle, or a 2-, 3-, or 4-pyridyl group, each of which may have one or more substituents.

8. The method according to claim 1, wherein $R^3$ represents an oxygen-containing heterocycle substituted by a phenyl group, or a 2-, 3-, or 4-pyridyl group.

9. The method according to claim 1, wherein W represents a 1-piperazinyl group, a 4-methyl-1-piperazinyl group, a 4-((dimethylamino)ethyl)-1-piperazinyl group, or a 4-((dimethyl amino)propyl)- 1-piperazinyl group.

* * * * *